(12) United States Patent
Chan et al.

(10) Patent No.: US 7,598,368 B2
(45) Date of Patent: Oct. 6, 2009

(54) COX5C-1 GENE INTRON FOR INCREASING EXPRESSION LEVEL IN CASSETTES, PLANT CELLS AND TRANSGENIC PLANTS

(75) Inventors: Raquel Lia Chan, Paraje el Pozo (AR); Daniel H. Gonzalez, Paraje el Pozo (AR); Graciela C. Curi, Paraje el Pozo (AR); Julieta Cabello, Paraje el Pozo (AR)

(73) Assignees: Universidad Nacional Del Litoral, Rosario, Santa Fe (AR); Consejo Nacional de Investigaciones Cientificas y Tecnicas, Rosario, Santa Fe (AR); Bioceres S.A., Rosario, Santa Fe (AR)

( * ) Notice: Subject to any disclaimer, the term of this patent is extended or adjusted under 35 U.S.C. 154(b) by 0 days.

(21) Appl. No.: 11/495,883

(22) Filed: Jul. 31, 2006

(65) Prior Publication Data

US 2007/0192895 A1      Aug. 16, 2007

(30) Foreign Application Priority Data

Dec. 15, 2005      (AR) .......................... P20050105268

(51) Int. Cl.
*C07H 21/04*      (2006.01)
*C12N 15/82*      (2006.01)
*C12N 5/04*      (2006.01)
*A01H 5/00*      (2006.01)

(52) U.S. Cl. ...................... 536/24.1; 435/419; 800/298; 800/295

(58) Field of Classification Search ....................... None
See application file for complete search history.

(56) References Cited

U.S. PATENT DOCUMENTS 5,294,593 A * 3/1994 Khan .......................... 504/100
6,037,523 A * 3/2000 Albertsen et al. ........... 800/287

OTHER PUBLICATIONS

Donald et al. Mutation of either G box of I box sequences profoundly affects expression from the *Arabidopsis* rbcS-1 promoter. (1990) EMBO J. vol. 9; pp. 1717-1726.*
Benfey et al. The Cauliflower Mosaic Virus 35S promoter: combinatorial regulation of transcription in plants. (1990) Science; vol. 250; pp. 959-966.*
Kim et al. A 20 nucleotide upstream element is essential for the nopaline synthase (nos) promoter activity. (1994) Plant Mol. Biol. vol. 24; pp. 105-117.*
Rounsley et al. *Arabidopsis thaliana* chromosome 2 clone T8I13 map CIC06C03, complete sequence. (2002) GenBank Accession AC002337, pp. 1-35.*
Welchen et al. The promoter of the *Arabidopsis* nuclear gene COX5b-1, encoding subunit 5b of the mitochondrial cytochrome c oxidase, directs tissue-specific expression by a combination of positive and negative regulatory elements. (2004) J. of Exp. Botany; vol. 55, pp. 1997-2004.*
Koziel et al. Optimizing expression of transgenes with an emphasis on post-transcriptional events. (1996) PMB; vol. 32; pp. 393-405.*
Callis, J., et al., "Introns increase gene expression in cultured maize cells," *Genes Dev.* 1:1183-1200, Cold Spring Harbor Laboratory Press (1987).
Carpenter, C.D., and Simon, A.E., "Preparation of RNA," *Meth. Mol. Biol. 82*: 85-89, Humana Press Inc. (1998).
Curi, G.C., et al., "The leader intron of *Arabidopsis thaliana* genes encoding cytochrome c oxidase subunit 5c promotes high level expression by increasing transcript abundance and translation efficiency," *J. Exp. Bot.* 56:9 pages, Epub (Aug. 2005).
Felitti, S.A., et al., "Expression of sunflower cytochrome *c* mRNA is tissue-specific and controlled by nitrate and light," *Physiol. Plant.* 99:342-347, Physiologia Plantarum (1997).
Grossman, L.I., and Lomax, M.I., "Nuclear genes for cytochrome *c* oxidase," *Biochim. Biophys. Acta 1352*:174-192, Elsevier Science B.V. (1997).
Hull, G.A., and Devic, M., "The β-Glucuronidase (*gus*) Reporter Gene System," *Meth. Mol. Biol. 49*:125-141, Humana Press (1995).
Kruger, N.J., "The Bradford Method for Protein Quantitation," in *Prot. Protocols Handbook*, Walker, J.M, ed., Humana Press Inc., Totowa, NJ, pp. 15-20 (1996).
Nakagawa, T., et al., "Separation, amino-terminal sequence and cell-free synthesis of the smallest subunit of sweet potato cytochrome *c* oxidase," *Eur. J. Biochem.* 165:303-307, FEBS (1987).
Nakagawa, T., et al., "Molecular cloning of a cDNA for the smallest nuclear-encoded subunit of sweet potato cytochrome *c* oxidase, Analysis with the CDNA of the structure and import into mitochondria of the subunit," *Eur. J. Biochem.* 191:557-561, FEBS (1990).
Nakagawa, T., et al., "The Nuclear Gene for Subunit Vc of Sweet Potato Cytochrome *c* Oxidase," *Plant Cell Physiol.* 34:621-626, Oxford University Press (1993).
Welchen, E., et al., "Metabolic regulation of genes encoding cytochrome *c* and cytochrome *c* oxidase subunit Vb in *Arabidopsis*," *Plant Cell Environ.* 25:1605-1615, Blackwell Publishing Ltd. (2002).
Baker, K.E. and Parker, R., "Nonsense-mediated mRNA decay: terminating erroneous gene expression," *Curr. Opin. Cell Biol. 16*:293-299, Current Science (2004).

(Continued)

*Primary Examiner*—Cathy Kingdon Worley
(74) *Attorney, Agent, or Firm*—Sterne, Kessler, Goldstein & Fox P.L.L.C.

(57) ABSTRACT

An isolated DNA molecule for enhancing gene expression of a coding sequence, fragment, genetic variant, cassette, vector, cell, plant and seed containing said molecule, wherein the molecule comprises introns for induce an increase in the expression level of a transgene, useful in DNA constructions for transforming plant cells, wherein the cell or plant has a construction containing one of these introns under control of a promoter and upstream of a coding sequence stably integrated in its genome displaying higher expression levels as compared to non-transformed cells or plants, or cells or plants transformed with constructions that lack the inventive intron, wherein the sequences of 5'-non-coding sequences of the genes mentioned above also comprise promoters and exonic sequences in DNA constructions displaying synergism with the effect produced by the intron, and wherein the 5'-non-coding sequences of COX5-c genes lacking said intron promote tissue-specific expression in pollen when they are comprised in DNA constructions for plant transformation.

13 Claims, 9 Drawing Sheets

OTHER PUBLICATIONS

Bolle, C., et al., "Intron sequences are involved in plastid- and light-dependent expression of the spinach *PsaD* gene," *Plant J.* 10:919-924, Blackwell Scientific Publishers (1996).

Christensen, A.H., et al., "Maize polyubiquitin genes: structure, thermal perturbation of expression and transcript splicing, and promoter activity following transfer to protoplasts by electroporation," *Plant Mol. Biol.* 18:675-689, Kluwer Academic Publishers (1992).

Clough, S.J. and Bent, A.F., "Floral dip: a simplified method for *Agrobacterium*- mediated transformation *of Arabidopsis thaliana*," *Plant. J.* 16:735-743, Blackwell Scientific Publishers (1998).

Curi, G.C., et al., "Genes encoding cytochrome *c* oxidase subunit 5c from sunflower (*Helianthus annuus* L.) are regulated by nitrate and oxygen availability," *Plant Sci.* 163:897-905, Elsevier Scientific Publishers Ireland Ltd. (2002).

Curi, G.C., et al., "Nuclear and mitochondrial genes encoding cytochrome *c* oxidase subunits respond differently to the same metabolic factors," *Plant Physiol. Biochem.* 41:689-693, Elsevier Science (2003).

Dickey, L.F., et al., "Light Regulation of *FED-1* mRNA Requires an Element in the 5' Untranslated Region and Correlates with Differential Polyribosome Association," *Plant Cell* 10:475-484, American Society of Plant Physiologists (1998).

Elorza, A., et al., "Nuclear *SDH2-1* and *SDH2-2* Genes, Encoding the Iron-Sulfur Subunit of Mitochondrial Complex II in *Arabidopsis*, Have distinct Cell-Specific Expression Patterns and Promoter Activities," *Plant Physiol.* 136:4072-4087, American Society of Plant Physiologists (2004).

Gidekel, M., et al., "The first intron of the *Arabidopsis thaliana* gene coding for elongation factor 1β contains an enhancer-like element," *Gene* 170:201-206, Elsevier Science (1996).

Grossman, L.I. and Lomax, M.I., "Nuclear genes for cytochrome *c* oxidase," *Biochim. Biophys. Acta* 1352:174-192, Elsevier Science (1997).

Hamanaka, S., et al., "Identification of cDNA encoding cytochrome *c* oxidase subunit 5c (COX5c) from rice: comparison of its expression with nuclear-encoded and mitochondrial-encoded *COX* genes," *Genes Genet. Syst.* 74:71-75, Genetics Society Of Japan (1999).

Heiser, V., et al., "The plant mitochondrial 22 kDa (PSST) subunit of respiratory chain complex I is encoded by a nuclear gene with enhanced transcript levels in flowers," *Plant. Mol. Bio.* 31:1195-1204, Kluwer Academic Publishers (1996).

Hir, H.L., et al., "How introns influence and enhance eukaryotic gene expression," *Trends Biochem. Sci.* 28:215-220, Elsevier Trends Journals (2003).

Huang, J., et al., "Flower-Enhanced Expression of a Nuclear-Encoded Mitochondrial Respiratory Protein Is Associated with Changes in Mitochondrion Number," *Plant Cell* 6:439-448, American Society of Plant Physiologists (1994).

Jänsch, L., et al., "New insights into the composition, molecular mass and stoichiometry of the protein complexes of plant mitochondria," *Plant J.* 9:357-368, Blackwell Scientific Publishers (1996).

Jefferson, R.A., et al., "GUS fusions: β-glucuronidase as a sensitive and versatile gene fusion marker in higher plants," *EMBO J.* 6:3901-3907, Oxford University Press (1987).

Jeon, J., et al., "Tissue-Preferential Expression of a Rice α-Tubulin Gene, *OsTubA1*, Mediated by the First Intron," *Plant Physiol.* 123:1005-1014, American Society of Plant Physiologists (2000).

Kadowaki, K., "Targeting presequence acquisition after mitochondrial gene transfer to the nucleus occurs by duplication of existing targeting signals," *EMBO J.* 15:6652-6661, Oxford University Press (1996).

Kosugi, S., et al., "Two of three promoter elements identified in a rice gene for proliferating cell nuclear antigen are essential for meristematic tissue-specific expression," *Plant J.* 7:877-886, Blackwell Scientific Publishers (1995).

Landschütze, V., "Mitochondrial citrate synthase from potato: predominant expression in mature leaves and young flower buds," *Planta* 196:756-764, Springer-Verlag (1995).

Lorković, Z., et al., "Pre-mRNA splicing in higher plants," *Trends Plant Sci.* 5:160-167, Elsevier Science (2000).

Mascarenhas, D., et al., "Intron-mediated enhancement of heterologous gene expression in maize," *Plant Mol. Biol.* 15:913-920, Kluwer Academic Publishers (1990).

McElroy, D., et al., "Isolation of an Efficient Actin Promoter for Use in Rice Transformation," *Plant Cell* 2:163-171, American Society of Plant Physiologists (1990).

Millar, A., et al., "Mitochondrial cytochrome *c* oxidase and succinate dehydrogenase complexes contain plant specific subunits," *Plant Mol. Biol.* 56:77-90, Kluwer Academic Publishers (2004).

Morello, L., et al., "A long leader intron of the *Ostub16* rice β-tubulin gene is required for high-level gene expression and can autonomously promote transcription both in vivo and in vitro," *Plant J.* 29:33-44, Blackwell Scientific Publishers (2002).

Mun, J., et al., "Petunia actin-depolymerizing factor is mainly accumulated in vascular tissue and its gene expression is enhanced by the first intron," *Gene* 292:233-243, Elsevier Science (2002).

Norris, S.R., et al., "The intron of *Arabidopsis thaliana* polyubiquitin genes is conserved in location and is a quantitative determinant of chimeric gene expression," *Plant Mol. Biol.* 21:895-906, Kluwer Academic Publishers (1993).

Nott, A., et al., "Splicing enhances translation in mammalian cells: an additional function of the exon junction complex," *Genes Dev.* 18:210-222, Cold Spring Harbor Laboratory Press (2004).

Ohtsu, K., et al., "Characterization and expression of the genes for cytochrome *c* oxidase subunit VIb (COX6b) from rice and *Arabidopsis thalania*," *Gene* 264:233-239, Elsevier Science (2001).

Plesse, B., et al., "Effects of the polyubiquitin gene *Ubi. U4* leader intron and first ubiquitin monomer on reporter gene expression in *Nicotiana tabacum*," *Plant Mol. Biol.* 45:655-667, Kluwer Academic Publishers (2001).

Ribichich, K., et al., "Cell-Type-Specific Expression of Plant Cytochrome *c* mRNA in Developing Flowers and Roots," *Plant Physiol.* 125:1603-1610, American Society of Plant Physiologists (2001).

Rose, A., "The effect of intron location on intron-mediated enhancement of gene expression in *Arabidopsis*," *Plant J.* 40:744-751, Blackwell Scientific Publishers (2004).

Rose, A. and Last, R.L., "Introns act post-transcriptionally to increase expression of the *Arabidopsis thaliana* tryptophan pathway gene PAT1," *Plant J.* 11:455-464, Blackwell Scientific Publishers (1997).

Simpson, G. and Filipowicz, W., "Splicing of precursors to mRNA in higher plants: mechanism, regulation and sub-nuclear organization of the spliceosomal machinery," *Plant Mol. Biol.* 32:1-41, Kluwer Academic Publishers (1996).

Smart, C., et al., "Cell-Specific Regulation of Gene Expression in Mitochondria during Anther Development in Sunflower," *Plant Cell* 6:811-825, American Society of Plant Physiologists (1994).

Trémousaygue, D., et al., "Internal telomeric repeats and 'TCPdomain' protein-binding sites co-operate to regulate gene expression in *Arabidopsis thaliana* cycling cells," *Plant J.* 33:957-966, Blackwell Scientific Publishers (2003).

Twell, D., et al., "Promoter analysis of gene that are coordinately expressed during pollen development reveals pollen-specific enhancer sequences and shared regulatory elements," *Genes Dev.* 5:496-507, Cold Spring Harbor Laboratory Press (1991).

Welchen, E., et al., "Metabolic regulation of genes encoding cytochrome *c* and cytochrome *c* oxidase subunit Vb in *Arabidopsis*," *Plant Cell Environ.* 25:1605-1615, Blackwell Scientific Publications (2002).

Wiegand, H.L., et al., "Exon junction complexes mediate the enhancing effect of splicing on mRNA expression," *Proc. Natl. Acad. Sci.* 100:11327-11332, National Academy of Science (2003).

Xu, Y., et al., "Rice Triosephosphate Isomerase Gene 5' Sequence Directs β-Glucuronidase Activity in Transgenic Tobacco but Requires an Intron for Expression in Rice," *Plant Physiol.* 106:459-467, American Society of Plant Physiologists (1994).

Voytas, D.F., et al., "The Structure, Distribution and Evolution of the Ta*1* Retrotransposable Element Family of *Arabidopsis thaliana*," *Genetics 126*:713-721, Genetics Society Of America (1990).

Yamamoto, Y., et al., "5'-Leader of a Photosystem I Gene in *Nicotiana sylvestris, psaDb*, Contains a Translational Enhancer," *J. Biol. Chem. 270*:12466-12470, American Society for Biochemistry and Molecular Biology (1995).

Zabaleta, E., et al., "Promoters of nuclear-encoded respiratory chain Complex I genes from *Arabidopsis thaliana* contain a region essential for anther/pollen-specific expression," *Plant J. 15*:49-59, Blackwell Scientific Publications (1998).

* cited by examiner

FIGURE 7

1) COX5c-1 Promoter (At2g47380) SEQ N°1

GAATTCAATACGAATAGTTACATTTTGTATTTTTGATTACTGTTGTTTCATGTTTGTACCTTTTTACCAATTTAATGCCC
TATACTATTTCCGTTGAAGCTTTAAATTCACAAGTTGGTTATATATTAGGTGAGCTGAAAATATCATTTGGGCCATTTAC
TTCATACAGTTGAGAAAATATTCAATTTGACACGTTTTTTTTTAATATAGTTGTATCGTGTTTTCTTATTTATTAGAATT
AATTTCTGTCAATATAATAATTTGTGGTTTTGCTTTCTTTGGGTCGCATCAAATGTTAGGTGTTTTGAAATTTTGATGAT
ATTATTATTTTTAGACAAAATTGACTGGAGTTGAACAGTAATGGGCCGGTCTCAGATGTTAGCCCAATAGGTTGACAGAG
AAAATGTATGATCCATGAGAGTGACTAAATTAAATTGATTAATCTCTTGCGCACACCTGAATCCTCGTCT

2) COX5c-1 Exon 1 SEQ N°:2

TCATTCGTTCCGGTCGTCGTCTACACCTCCACACTCCGACTTG

3) COX5c-1 Intron SEQ N°:3

GTAAATCCCCAGACTCATCTCTCTCTCCTTTTCTTTTGATTTCTAGATTTGCTAGTTTGTTTCGATTGTTCTTCTAGA
TAGAAATTAACGAGTGATTTTTGATTTAACCGATTCGCATCAATGCCCCTTCTTCTTATTGCGTCGATCTCATGGATCGG
GATCCATCGTTCCTCTATCTGATTTCTCTTGTGGGAAAGAATTTCAAGCTTTATGGTTTTGTAGTAATGAACGTTTATCA
TTTTCGTTCGAGGGAAGATTTTTAAACTTTCGTTATGCGGATTCTGGATATTAGGCTGTTTTTTTTTTTTTTTTAATC
GATTGAAGGATGTCAATTTATAGATTGGGCTGTAGATTGCTAGTTTATGTCATTGATATTGAATTGTAAGTTTTTCGATC
TTCCAGTCATACAAATCACTAATTGCCTCAAGATAGGAAAATCCATTGGCAGTATATAGATGGAGTTCATATCTTAAGCA
CAGGTTTATATGGTCATTACATTTCTAGCTTTTGTTTGTTAGGACTGATTCATGTTGGGTTTTGGGGTTATTCTTTATA
ACGGGTCATGCTTGTATATATGTAGTATCAATACATTTCTGATTTGTGGTTATGCTTGATGCAAAAAAGATCCAATCTTT
CGAGTTGGTAGTGAGTTACATTTGTTACTTTTGGTAG

4) COX5c-1 Exon 2 non-coding region SEQ N°:4

GTTGAGAAGAAGAAAGAAGAG

FIGURE 8

5) COX5c-2 Promoter (At3g62400) SEQ N°:5

GAATTCCACAGTGCATTTATAATCCTAGTCAAGTACACAAACATGACATTAACACAACCACACGCCTGAAATACACTTAA
TGGTCCATTAAGATTAAAGTCATATTGTACCACGAAACGGAAGCTATAATTCCCTTTCTCTTTGGTGATTCTTCGGTTGT
GCGTTTCGTATACTCTCTTGGGATCTTTAACAGCTTGAAACAACAAACAAAGCATAGATTCCCATTGGTTCCTATTAATT
GAATCTCCAACGAACACTAGCCTCTTGCCTCTAATCATTTCCAGCATCTTTGTAGCATTGAACCTAAACTCACACATACC
ACAATTTCCAATTCAGGACCATGAATTGCATTCCTACTTATTCAGAGAGATTAAGTGCTCAGTGGAACTATGAATCCCAC
TTATCATCATCAGTCACTATCACCAACCACTACTACTTCAATAGAGAGATCTTCTTAAAGGCCTACGAGGAAAACAACAA
AATTAGAAAGAAGAAATTAAACCTGGGAGCATGACAATCCTGAGGCTCCCATCTCCAATTCATGTAATTAAGATCCAATC
TTCCATTGCTTTGACAACCAAATTCCTTCATCGATAAAACTAGCCTATGAATCCACATGGCAAAAGAGGACAAGACGCATT
TGTGTACAATGGATAATCACTATCGTAAACCCACTTCCCTTTCGTAACATCACATTCTTCGATTCTCTTCTCTGTCTTCT
TATCTTCACCATTGTTGCTCGGAAGTTCAATCACTTTAATCGAAGTTAAATTAGCAATTTCCCTAACTTCCTTAACCAAA
CTCTCGCCGCTAATCTTCTGCTCAAAAACAGAAATTTTTGAAGACCCGGAAGTGTTTTCGGGTGAATTGAAATGGGTAGA
GATCAGAATCGGACTTGCTTGAGGAGAAACTGAAGAATCGGAAATGGCGGCAATAGGGCTTAAATCGATCTGGAAGTTAG
CTTCTGGTGTTGGGTAAAGAGAAGAGTTAGATTTGAGTAAGGAAGAGGAGAAGAAAGTGAAGAAAACAATGGCGGAAGAG
ATTATTGTGATGATGAATGCTAAGACTCTTGTGGACTTCACAGAGAAACTTCTTTGTCTCTCCATCTTCTATCTCTTTAT
TTATTTTTTCTCTGTAACTGTTATAAGTTAGTTAAGAAAAAACAGTTTCATAATTATCTGTAATCAGAGAGAAATTTGAAAT
CGAAAAATGGAACTGTTTGAGAAAAGGATTGAAATTTTGGAGTCGACAAAGGTGGTTGAATTAGTGGGGTATAGAGGAGA
GATTCGGTGAAGAAATGATAATGACGTTCTTACAAACTCGTGAGCTCATGAATTTTACAATAATTAACGGAACAGAGGGA
AAGATAATGATTATTTAAAAAAGTTCAGGATTAGGAAATTAGTTTAGTGTGTTGACAGATTGGATTTGGCATTATTAACG
TGGTGGGACACACTCGGGGAACACGAGCAGCGAATGGTTTACTTTTTTAAAAAGCAAATTCCATAAAATGCCCATTGAAG
AAATAAGAGATCAGGCCCATGTTTAAGGCCCAATAAGACACAAATGGAGTAGAGAAGTGATTATCTGCTTACGCAACTTC
TTCAATCACCCACCATT

6) COX5c-2 Exon 1 SEQ N°:6

TCGTTTTCGTCGTGAGCTTCTGTCTCGTTCATCTACACAATCTGACTCG

7) COX5c-2 Intron SEQ N°:7

GTAAAGTCCATATTCTTCCCTTGATGATAATTGTTGTTTCCTTTATGATTTTGTGGTGATTTTCGTTATAGATAGGTGGC
GGATTGTGAAGTTACGATTAATTTTTATCAGATTCGAATCCATTTCTCGTTTTTTTTCCCGTGTAGATCGGTGTGCTTAA
GATCGGAATTTCTCGTTTAAATCTTCCGTTGATTTAGATTTGATGCTCTTAGTGTTGTGATGCTTTGAAACGTTAATCCT
TTTCTTCGGGAGAAATGCCAATTTTATTTTCAGTATCTGGATCCTGTGGATTAGGGTTCTTGTATCATTTTGGGAATAAA
TTCAAAGCCTTTGATATCTTCCTTTGAATAGAGACGTAGTTAAGAGGTTAGACAGAAAATGGATCGAAATTGTACATGTT
TATGTGTATATATAGACTCCAAGTGCAAACCAGTAGAAATTAAGAGATCAGGTAGATTAGTGTGTGTGTGTATAGATG
TTTTATTGGTTGTCAATAAAGTTTTCAGCTTTAGGAATCGTGAGCATTGTGAAAGTATCAATTATGTTAGTATTGACTCT
ATGATTAAAATGTGTGCTAG

8) COX5c-2 Exon 2 non-coding region SEQ N°:8

GTTGAGAAGAA

FIGURE 9

9) COX5c-3 Promoter (At5g61310) SEQ N°:9

AAGAGATGGGAAGAGTTTCTTACGTTCAGGAGAGAACACAAGAACGTCTTGCTTCCGTTGATTCGTTCCCGGAGAAAGAT
CATGATCGAATCTAAAGATTCCGGTAAAGAATACATACAATCGTATGTAGATACTCTGCTCGATCTTGAGCTTCCTGATG
AGAAGAGGAAACTAAACGAAGACGAGATCGTGAGTTTATGCTCTGAGTTTCTCAACGCCGGGACTGATACAACAGCGACG
ACACTTCAATGGATAATGGCGAATCTGTGAGAAACCAGGAAATTCAAAAGAGGTTATACGAAGAGATAAAAAGTGTAATC
GGTGAAGAAGAAGAGAAGGAGATTGAAGAAGAAGAGATGAAGAAGATGCCGTATCTTAAAGCTGTCGTGTTAGAAGGTCT
CCGGTTACATCCACCGGGACATTTGTTGTTACCACACAGAGTAAGTGAAGACACTGAGCTAGGAGGATACAGAGTTCCAA
AGAAAGGGACGTTTAATATCAATGTGGCGATGATAGGGAGAGATCCAACAGTGTGGGAGGAGCCAATGGAGTTTAAGCCG
GAGAGATTCATCGGAGAAGATAAAGAAGTTGATGTTACTGGAAGTAGAGGGATAAAGATGATGCCGTTTGGAGCAGGAAG
GAGGATCTGTCCAGGGATTGGATCGGCCATGTTGCATTTGGAGTATTTTGTGGTGAATTTGGTTAAAGAGTTTGAGTGGA
AAGAAGTTGAAGGTTATGAAGTTGACTTGTCTGAGAAATGGGAGTTCACTGTTGTTATGAAGTATCCTCTTAAAGCTCTT
GCTGTGACAAGAAGGAAGGAGAAGACACATATCGTCATGGCTTAGAGACAGAGTAGCAGATTGATTTCTTGGGGATGTTT
TTGTTCTTTAGTTTTTCAGTTTTTTTTTTTTGGTTTTCTAGAGTGTTTTTGGTTCAATCTGTTGTGGTAGAAACGTTG
TCGTTTCAATAAAGGCAGCCATTTATTGAAACGTTGTCGTTTAGATGCCTCTCATTTTTGTTGAAAGCCCTAGAAAATGG
AATTAGACGTATAAATTGATTTCATCTTTCTCAGCTTTTGCT

10) COX5c-3 Exon 1 SEQ N°:10

AAACGCAGATAAACAGGTTTCTTTCTGATTCTTCTTCGTATTGGAACATACAATTATACAATTGG

11) COX5c-3 Intron SEQ N°:11

GTATAACCATTTTCTTGGATTTCAGTGTATGATTCCTTTTAATGTTCAAAGTTCTCTGCTTTCTCTTGCGTAATTTTGCT
CTCTGTTTTTTTTTGTCTTCATCTGTATAATGGAATCTCCCGAAAAAACTCGAAGTTTATAAACTGGATTGATTCCTTT
CTTCTCCATTGTGGTCTTAGGTTTCGAAAGTTTCTCACTTTAGACTTGTGTTAGCTCTAGAATGCTTGTATGATATGTTT
GTGACATTGTGGTGGAGATGATGAATGTTAAGTAAAAGGTCTGAGTAGGTTATGAGTAAAGTGTGTAGCTTTTGATTTTA
ATTTAGTTTCGAGGAGACAATTTTTTAACTTAATAGGAGAGGGCCCTTGTCCATGCCTTGAGTCATGGCATCTGTGGCTC
CGCAACCTCTCCAACAATGAACCTGATTCACCACGTGCTTGTGTGTGCAATCTGATGGGTCGATTTTTAAAGGCTTGGGG
TTGCTTTCTATTATTGATTGCCAATCTAGAATTCTCCCTATATACATTGGTCTCCTTGTGCTTCTTTATCATCAATTAGC
TGCCCTCATAAGTCCTGCACTGATCAAAGACCTCCTTGACTGATCCACGCGAAAGTATCTAAATAGTTCTTTGTATTGCT
ATGTTGAAGTTTGAAGCTTTTTGACAAAGCTTGTTTGATATAGGCATTGCTTGTGGATGATGTTTATGATTCCCTCATTA
TTGTATGTGTGGACTACAGAACTATTCATGTATTAGCATTTACCCTTTTGTGGTTAAGCTGAAGAAGTATACCATACCTT
CTAGTGTTTGTTTGATTGGGTTTTTCACTGTGGCCATTAGAGTGTTTAAGATAAGTACTCTGTTTGTCGATACTCTAGGA
TCTCTCTTTCAAGTGGGTTTGATTTGAAGACGTATTATATGTGTATATATAACCGAAGAATAATGTTATGTTTTGCTAAA
TGTTGATGTTTAGATTATCAAAGAGAATGGATTTTTGTATATTCATGATCTATTGCAATGTTTGATTGGTTTAG

12) COX5c-3 Exon 2 non-coding region SEQ N°:12

TGTGAGCAGGAGAGTGGCAAAGAG

COX5C-1 GENE INTRON FOR INCREASING EXPRESSION LEVEL IN CASSETTES, PLANT CELLS AND TRANSGENIC PLANTS

BACKGROUND OF THE INVENTION

1. Field of the Invention

The present invention relates to biotechnology field, more specifically to genetic engineering in plants. The invention provides useful DNA sequences and constructions to regulate recombinant gene expression in plants. More specifically, the invention provides new regulatory sequences derived from *Arabidopsis thaliana* COX5c-1, COX5c-2 and COX5c-3 genes.

2. Description of the Prior Art

Genetic engineering in plant biotechnology made an amazing advance in the fields of research and production of new products.

Research in genetic engineering requires access to a wide variety of sequences that are useful for the regulation of transgenes. There are two examples of such elements: introns and promoters.

Selection of promoters controlling or directing transcription levels of one or more genes is one of the greatest challenges that molecular biology must achieve for the success of plant biotechnology.

Therefore, many efforts have been made in the last two decades to find promoters and other sequences capable of guaranteeing the expression according to the needs of each transgene. Several promoters of different species have been studied for production of transgenic plants; including vegetal, viral, from the Ti and Ri plasmids of *Agrobacterium tumefaciens*, as well as natural exons and introns, namely the first intron of maize alcohol dehydrogenase-1 (Callis et al., 1987) or the first exon/intron of rice actin-1 gene (McElroy et al., 1991).

Gene transcription is regulated by a promoter region (cis element) and multiple regulatory proteins (trans elements). A genetic engineering project requires the simultaneous use of several promoters. A first promoter can be used upstream of the gene of interest, while a second promoter can be used to express a selection marker.

Eukaryotic genes are usually interrupted by non-coding sequences, the introns. Eukaryotic genes are first transcribed as pre-RNA, which contain introns within their sequences. Introns are then removed during the splicing, the final product, the mRNA, can be translated to a protein.

It has been shown that introns are involved in the regulation of gene expression in plants. The first intron of maize enzyme alcohol dehydrogenase-1 (Adh-1) gene is capable of increasing transcription in anaerobiosis (Callis et al., 1987). Although in a smaller degree, the intron also stimulates transcription in aerobic conditions. It has been proposed that the enhancement of gene expression is due to pre-RNA stabilization produced by the introns. Remarked increases have also been reported in the expression of gene CAT (from 12 to 20 times) when the first intron of the maize dehydrogenase alcohol (Mascarenhas et al, 1990). It has also been reported that these effects are produced at the transcription level.

Naturally occurring introns with their adjacent sequences have been employed to increase transcription, especially when intron is located near the 5' end of the gene. It has also been reported that potentiation of intron-mediated mRNA accumulation (IME) depends on intron origin, exonic regions flanking said intron and cell type. Molecular mechanisms underlying IME have not been completely elucidated (Simpson et al., 1996; Lorkovic et al., 2000).

Enhancement of expression by introns has been reported for several genes from maize and other monocots (see WO98/5921, and also see Callis et al., 1987; McElroy et al., 1990; Christensen et al., 1992; Xu et al., 1994; Jeon et al., 2000; Morello et al., 2002) and dicot plants (Norris et al., 1993; Gidekel et al., 1996; Rose and Last, 1997; Plesse et al., 2001; Mun et al., 2002). Introns influencing expression are more frequently located near the translation start site within non-coding regions, as is the case for COX5c genes. The exact role of introns in promoting an increase in expression levels is not clear. Some introns seem to contain transcriptionally active regulatory elements (Gidekel et al., 1996), while others seem to act post-transcriptionally (Rose and Last, 1997), suggesting the existence of different mechanisms of action. It has recently been proposed that many introns would act by increasing the processivity of the transcription machinery (Rose, 2004). Besides the quantitative enhancement of expression, some introns direct tissue-specific patterns of expression (Bolle et al., 1996; Jeon et al., 2000). In some cases, like those of the Petunia actin-depolymerizing factor (Mun et al., 2002), the rice α-tubulin OstubA1 (Jeon et al., 2000) and the *Arabidopsis* polyubiquitin Ubi1 y Ubi4 genes (Plesse et al., 2001), expression is specifically observed in vascular tissues and/or metabolically active dividing cells. These expression patterns are similar to those observed here for the COX5c genes, probably indicating that these introns operate with similar mechanisms or respond to similar factors.

Although the involvement of introns in translation seems an unexpected consequence, similar observations have been made in animal and plant systems (Le Hir et al., 2003; Rose, 2004). It has been proposed that increment in translational efficiency by introns is related to the location of proteins near the exon-exon junctions during splicing that subsequently increase the interaction of ribosomes with the mRNA (Wiegand et al., 2003; Nott et al., 2004).

Cytochrome c oxidase (COX) is a multimeric complex composed of several different subunits, two or three of them encoded by the mitochondrial genome and the rest encoded in the nucleus (Grossman et al., 1997; Jänsch et al., 1996).

Three different nuclear-encoded subunits, COX5b, COX6a, and COX6b, have been identified in plants through sequence comparisons with yeast and animal counterparts (Kadowaki et al., 1996; Ohtsu et al., 2001; Curi et al., 2003).

A fourth subunit, COX5c, is the smallest COX plant subunit and has been discovered by protein purification studies (Nakagawa et al., 1987, 1990). Recent studies using 2D gel electrophoresis combined with mass spectrometry indicated the presence of additional plant-specific subunits (Millar et al., 2004).

COX5c is a polypeptide of about 63 amino acids with sequence similarity to yeast COX VIIa and mammalian COX VIII (Nakagawa et al., 1990). COX5c cDNAs have been isolated from sweet potato, rice, and sunflower (Nakagawa et al., 1990; Hamanaka et al., 1999; Curi et al., 2002), and ESTs from several species are available. The first COX5c gene was also isolated from sweet potato (Nakagawa et al., 1993), and related sequences could be detected in the totally or partially sequenced genomes from *Arabidopsis*, rice, and *Lotus corniculatus*. Expression studies in rice and sunflower indicated that COX5c genes are expressed at different levels throughout the plant (Hamanaka et al., 1999; Curi et al., 2002). However, no detailed analysis on tissue specificity of expression or on the gene sequences involved in directing this expression have been performed by any plant COX5c gene.

It is generally assumed that the expression of components of the plant mitochondrial respiratory chain must somehow be co-ordinated. It is now well established that most mitochondrial components show enhanced expression in flowers (Huang et al., 1994; Landschütze et al., 1995; Felitti et al., 1997; Heiser et al., 1997; Zabaleta et al., 1998). Expression in flowers is mainly localized in anthers as indicated by in situ hybridization experiments (Smart et al., 1994; Ribichich et al., 2001; Elorza et al., 2004). Expression studies in *Arabidopsis thaliana* have shown similar responses for the nuclear genes encoding cytochrome c and COX subunits 5b, 6a, and 6b (Welchen et al., 2002; Curi et al., 2003). Notably, a different behaviour has been observed for genes encoding COX subunit 5c (COX5c), at least in sunflower (Curi et al., 2002). However, no functional studies have been performed on the cis-acting sequences required for the expression of COX5c genes from any species.

SUMMARY OF THE INVENTION

It is therefore an object of the invention to provide an isolated DNA molecule comprising at least one of the following introns: COX5c-1 gene intron, as shown in SEQ No 3, preferably from nucleotides 22 to 698 from the start codon of COX5c-1; COX5c-2 gene intron, as shown in SEQ No 7, preferably from nucleotides 12 to 591 from the start codon of COX5c-2; COX5c-3 gene intron, as shown in SEQ No 11, preferably nucleotides 25 to 1058 from the start codon of COX5c-3; or a portion thereof, namely a fragment, genetic variant or deletion of at least one of said sequences that conserve the capability of enhancing gene expression in plant cells when it is located in a construction under control of a non-related promoter and upstream of at least one coding sequence.

It is still another object of the present invention to provide an isolated DNA molecule comprising at least one of the following sequences: COX5C-1 promoter-exon 1-intron-exon 2, SEQ No 1-2-3-4, preferably from nucleotides 1 to 1211 of Cox5C-1; COX5C-2 promoter-exon 1-intron-exon 2, SEQ No 5-6-7-8, preferably from nucleotides 1 to 1153 from Start Codon upstream to non coding region of Cox5C-2; COX5C-3 promoter-exon 1-intron-exon 2, SEQ No 9-10-11-12, preferably from nucleotides 1 to 2205 of Cox5C-3; or a portion thereof, namely a fragment, genetic variant or deletion of at least one of said sequences that conserve the capability of enhancing gene expression of at least one coding sequence of a gene of interest.

It is a further object of the present invention to provide an isolated DNA molecule comprising at least one of the following sequences: COX5c-1 gene exon 1-intron-exon 2, SEQ No 2-3-4, preferably from nucleotides 1 to 741 from the start codon of Cox5C-1; COX5c-2 gene exon 1-intron-exon 2, SEQ No 6-7-8, preferably from nucleotides 1 to 640 from the start codon of Cox5C-2; COX5c-3 gene exon 1-intron-exon 2, SEQ No 10-11-12 preferably from nucleotides 1 to 1123 from the start codon of Cox5C-3, or a portion thereof, namely a fragment, genetic variant or deletion of at least one of said sequences keeping the capability of enhancing gene expression in plant cells when it is located in a construction under control of a non-related promoter and upstream of at least one coding sequence of interest.

It is a further object of the present invention to provide an isolated DNA molecule comprising at least one of the following sequences: COX5c-1 promoter-exon 1-exon 2, SEQ No:1-2-4, preferably from base 1 to 21 upstream of the start codon of COX5c-1 linked to the sequence from base 699 to 1211 downstream of the start codon of COX5c-1; COX5c-2 promoter-exon 1-exon 2, SEQ No:5-6-8, preferably from base 1 to 11 upstream of the start codon of COX5c-2 linked to the sequence from base 592 to 1153 of the start codon of COX5c-2; COX5c-3 promoter-exon 1-exon 2, SEQ No:9-10-12, preferably from base 1 to 24 upstream of the start codon of COX5c-3 linked to the sequence from base 1059 to 2205 upstream of the start codon of COX5c-3; or a portion thereof, namely a fragment, genetic variant or deletion of at least one of said sequences keeping the capability of enhancing tissue-specific gene expression in plant cells when some of these sequences is located upstream of at least one heterologous coding sequence of a gene of interest.

It is therefore an object of the invention to provide an isolated DNA molecule comprising at least one of the following introns: COX5c-1 gene intron, as shown in SEQ No 3, preferably from nucleotides 22 to 698 from the start codon of COX5c-1; COX5c-2 gene intron, as shown in SEQ No 7, preferably from nucleotides 12 to 591 from the start codon of COX5c-2; COX5c-3 gene intron, as shown in SEQ No 11, preferably nucleotides 25 to 1058 from the start codon of COX5c-3; or a portion thereof, namely a fragment, genetic variant or deletion of at least one of said sequences that conserve the capability of enhancing gene expression in plant cells when it is located in a construction under control of a non-related promoter and upstream of at least one coding sequence, and wherein the molecule includes at least 100 consecutive bases with a homology of 80% with 100 consecutive bases of the sequence between nucleotides 22 and 698 when the sequence is SEQ ID No 3; at least 100 consecutive bases with a homology of 80% with 100 consecutive bases of the sequence between nucleotides 12 and 591 when the sequence is SEQ ID No 7; and at least 100 consecutive bases with a homology of 80% with 100 consecutive bases of the sequence between nucleotides 25 and 1058 when the sequence is SEQ ID No 11.

It is still another object of the present invention to provide an isolated DNA molecule comprising at least one of the following sequences: COX5C-1 promoter-exon 1-intron-exon 2, SEQ No 1-2-3-4, preferably from nucleotides 1 to 1211 of Cox5C-1; COX5C-2 promoter-exon 1-intron-exon 2, SEQ No 5-6-7-8, preferably from nucleotides 1 to 1153 from Start Codon upstream to non coding region of Cox5C-2; COX5C-3 promoter-exon 1-intron-exon 2, SEQ No 9-10-11-12, preferably from nucleotides 1 to 2205 of Cox5C-3; or a portion thereof, namely a fragment, genetic variant or deletion of at least one of said sequences that conserve the capability of enhancing gene expression of at least one coding sequence of a gene of interest, and wherein the molecule includes at least 100 consecutive bases with a homology of 80% with 100 consecutive bases of the sequence between nucleotides 1 and 1211 when the sequence is SEQ ID No 1-2-3-4; at least 100 consecutive bases with a homology of 80% with 100 consecutive bases of the sequence between nucleotides 1 and 1153 when the sequence is SEQ ID No 5-6-7-8; and at least 100 consecutive bases with a homology of 80% with 100 consecutive bases of the sequence between nucleotides 1 and 2205 when the sequence is SEQ ID No 9-10-11-12.

It is a further object of the present invention to provide an isolated DNA molecule comprising at least one of the following sequences: COX5c-1 gene exon 1-intron-exon 2, SEQ No 2-3-4, preferably from nucleotides 1 to 741 from the start codon of Cox5C-1; COX5c-2 gene exon 1-intron-exon 2, SEQ No 6-7-8, preferably from nucleotides 1 to 640 from the start codon of Cox5C-2; COX5c-3 gene exon 1-intron-exon 2, SEQ No 10-11-12 preferably from nucleotides 1 to 1123 from the start codon of Cox5C-3, or a portion thereof, namely a fragment, genetic variant or deletion of at least one of said sequences keeping the capability of enhancing gene expression in plant cells when it is located in a construction under control of a non-related promoter and upstream of at least one coding sequence of interest, and wherein the molecule includes at least 100 consecutive bases with a homology of 80% with 100 consecutive bases of the sequence between nucleotides 1 and 741 when the sequence is SEQ ID No 2-3-4; at least 100 consecutive bases with a homology of 80% with 100 consecutive bases of the sequence between nucleotides 1 and 640 when the sequence is SEQ ID No 6-7-8; and at least 100 consecutive bases with a homology of 80% with 100 consecutive bases of the sequence between nucleotides 1 and 1123 when the sequence is SEQ ID No 10-11-12.

It is a further object of the present invention to provide an isolated DNA molecule comprising at least one of the following sequences: COX5c-1 promoter-exon 1-exon 2, SEQ No:1-2-4, preferably from base 1 to 21 upstream of the start codon of COX5c-1 linked to the sequence from base 699 to 1211 downstream of the start codon of COX5c-1; COX5c-2 promoter-exon 1-exon 2, SEQ No:5-6-8, preferably from base 1 to 11 upstream of the start codon of COX5c-2 linked to the sequence from base 592 to 1153 of the start codon of COX5c-2; COX5c-3 promoter-exon 1-exon 2, SEQ No:9-10-12, preferably from base 1 to 24 upstream of the start codon of COX5c-3 linked to the sequence from base 1059 to 2205 upstream of the start codon of COX5c-3; or a portion thereof, namely a fragment, genetic variant or deletion of at least one of said sequences keeping the capability of enhancing tissue-specific gene expression in plant cells when some of these sequences is located upstream of at least one heterologous coding sequence of a gene of interest, and wherein the molecule includes at least 100 consecutive bases with a homology of 80% with 100 consecutive bases of the sequence SEQ ID No 1-2-4; at least 100 consecutive bases with a homology of 80% with 100 consecutive bases of the sequence SEQ ID No 5-6-8; and at least 100 consecutive bases with a homology of 80% with 100 consecutive bases of the sequence SEQ ID No 9-10-12.

It is another object of the present invention to provide a construction comprising from 5' to 3': a) a plant functional promoter, b) a COX5c intron, c) a coding sequence, d) a 3'UTR.

It is another object of the present invention to provide a construction comprising from 5' to 3': a) a COX5c promoter-exon 1-intron-exon 2, b) a coding sequence, c) a 3'UTR.

It is another object of the present invention to provide a construction comprising from 5' to 3': a) a plant functional promoter, b) a COX5c gene exon 1-intron-exon 2, c) a coding sequence, d) a 3'UTR.

It is another object of the present invention to provide a construction comprising from 5' to 3': a) a COX5c promoter-exon 1-exon 2, b) a coding sequence, c) a 3'UTR.

It is a further object of the present invention to provide a plant and its descendant that contain in at least one of its cells the sequences named above, an active fragment, deletion or genetic variant thereof, under control of a plant functional promoter, wherein the plant is a monocot or a dicot plant, and it belongs to a species of a group consisting of rice, maize, wheat, alfalfa, soy, tobacco and cotton.

It is a still another object of the present invention to provide a DNA molecule capable of hibridizing in astringent conditions with at least one of the sequences mentioned above.

The above and other objects, features and advantages of this invention will be better understood when taken in connection with the accompanying drawings and description.

BRIEF DESCRIPTION OF THE DRAWINGS

The present invention is illustrated by way of example in the following drawings wherein.

(A) Scheme of the six sequenced COX5c genes available in data banks: three genes from *Arabidopsis thaliana* (AtCOX5c) and one each from *Ipomoea batatas* (IbCOX5c), *Oryza sativa* (OsCOX5c), and *Lotus corniculatus* (LcCOX5c). All genes contain a single intron (white boxes) located in the 5'-non-coding region. The OsCOX5c intron is not drawn to scale due to its length (2.4 kbp). Non-coding and coding regions of exons are shown in light and dark grey, respectively.

(B) Scheme of the different constructs used to analyse COX5c regions required for expression. Different regions of the COX5c-1 and COX5c-2 genes, containing 5'non coding region (black boxes), non coding regions of exons 1 and 2 located upstream of the start codon (light grey boxes), and the leader intron (white box) were fused to the gus coding region and introduced into plants. In a similar way, COX5c-2 untranslated leader sequences were fused to the COX5b-1 promoter (striped boxes) in both orientations.

Figure 2:
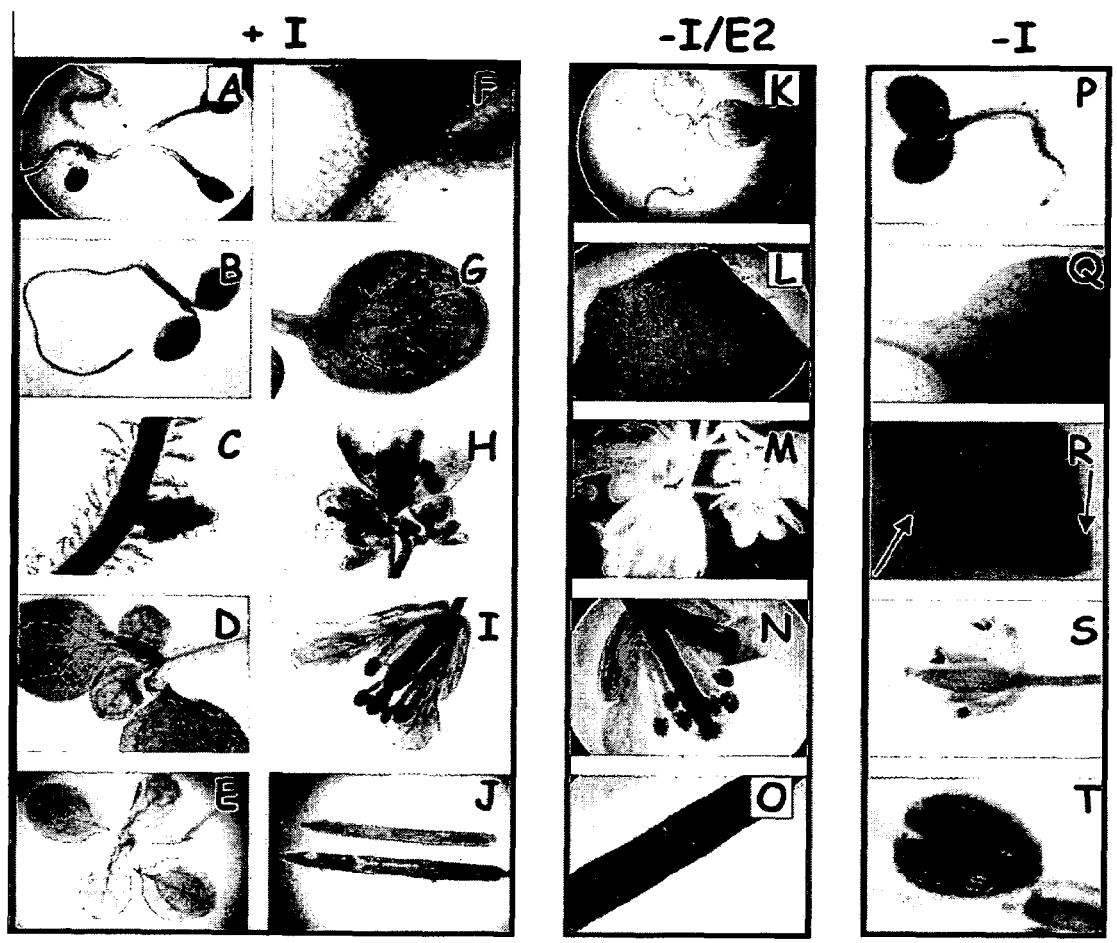

FIG. 2 shows histochemical localization of GUS activity in *Arabidopsis* plants transformed with constructs carrying different portions of the COX5c-2 gene fused to gus. Plants transformed with fragments containing non-transcribed upstream regions plus either the complete transcribed 5'-non-coding region (A-J), only exon 1 sequences (K-O), or the 5'-non-coding region without the intron (P-T) were analysed. Two-(A), 3-(B, K, P), 15-(D, F), and 20-d-old plants (C, E) are shown. Leaves (G, L, Q, R), flowers (H, I, M, N, S), anthers (T), and siliques (J, O) from adult plants are also shown.

Figure 3:
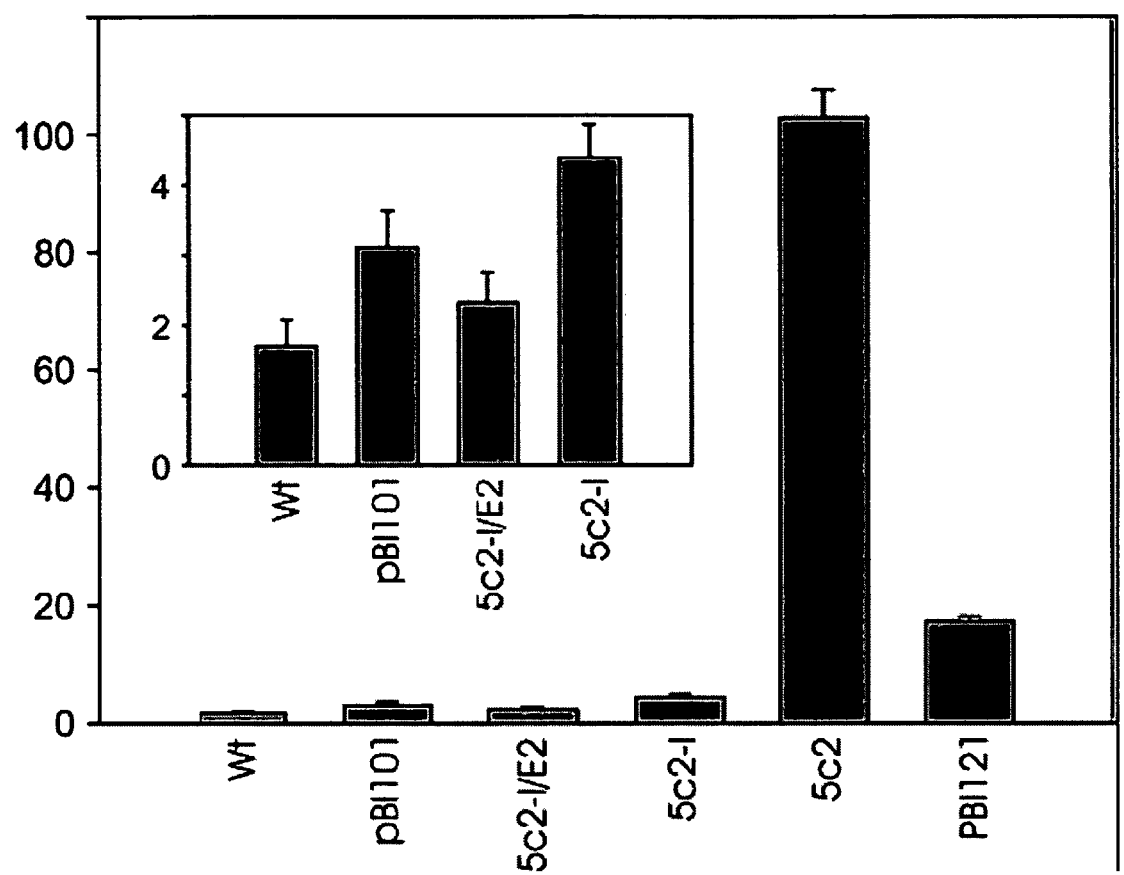

FIG. 3 shows bar-graphic illustrating that removal of the COX5c intron produces a pronounced decrease in expression of the reporter gene. GUS-specific activity of extracts from plants transformed with construct pBI5c2 (5c2+I) or the respective constructs in which either the intron plus a portion of exon 2 (5c2-I/E2) or only the intron (5c2-I) were removed was measured using the fluorogenic substrate MUG and protein extracts prepared from rosettes of 20-d-old plants. GUS activity was also measured in extracts from non-transformed plants (wt) or from plants carrying the promoterless gus gene (pBI101) or the gus gene under the control of the CaMV 35S promoter (pBI121). Error bars represent SE of three independent measurements with one representative line from each construct. Similar results were obtained with different independent lines. The inset shows an enlargement of the bars corresponding to plants that display low GUS activity values.

Figure 4:
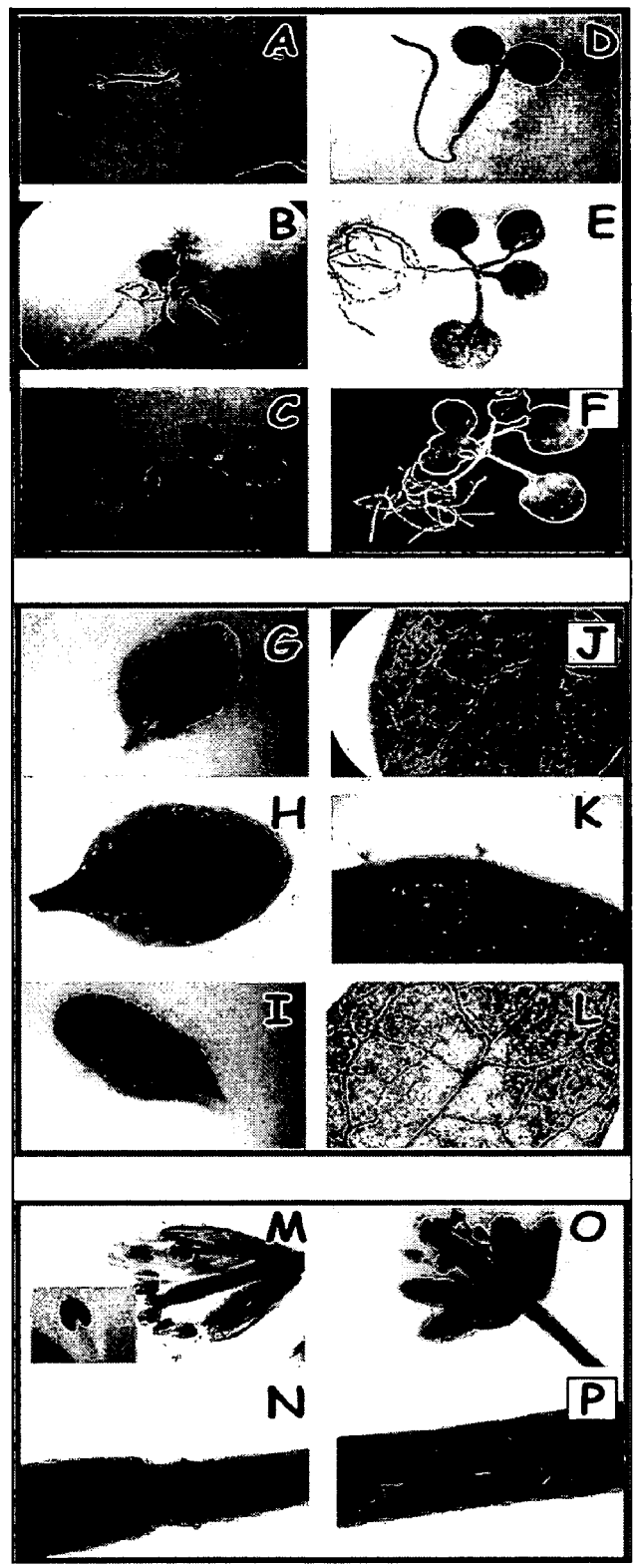

FIG. 4 shows histochemical localization of GUS activity in *Arabidopsis* plants transformed with the COX5b-1 promoter fused to the COX5c-2 leader intron. (A, B) Three- and 15-d-old plants transformed with a 609 bp COX5b-1 promoter fragment. (C-F) Similar plants transformed with the same promoter fragment fused to the COX5c-2 leader intron in the sense (D, E) or antisense (C, F) orientation. (G-L) Leaves from adult plants carrying the promoter alone (G, J) or with the intron in the sense (H, K) or the antisense (I, L) orientation. (M-P) Flowers and siliques from plants transformed with the COX5b-1 promoter fragment without (M, N) or with the COX5c-2 intron (O, P).

Figure 5:
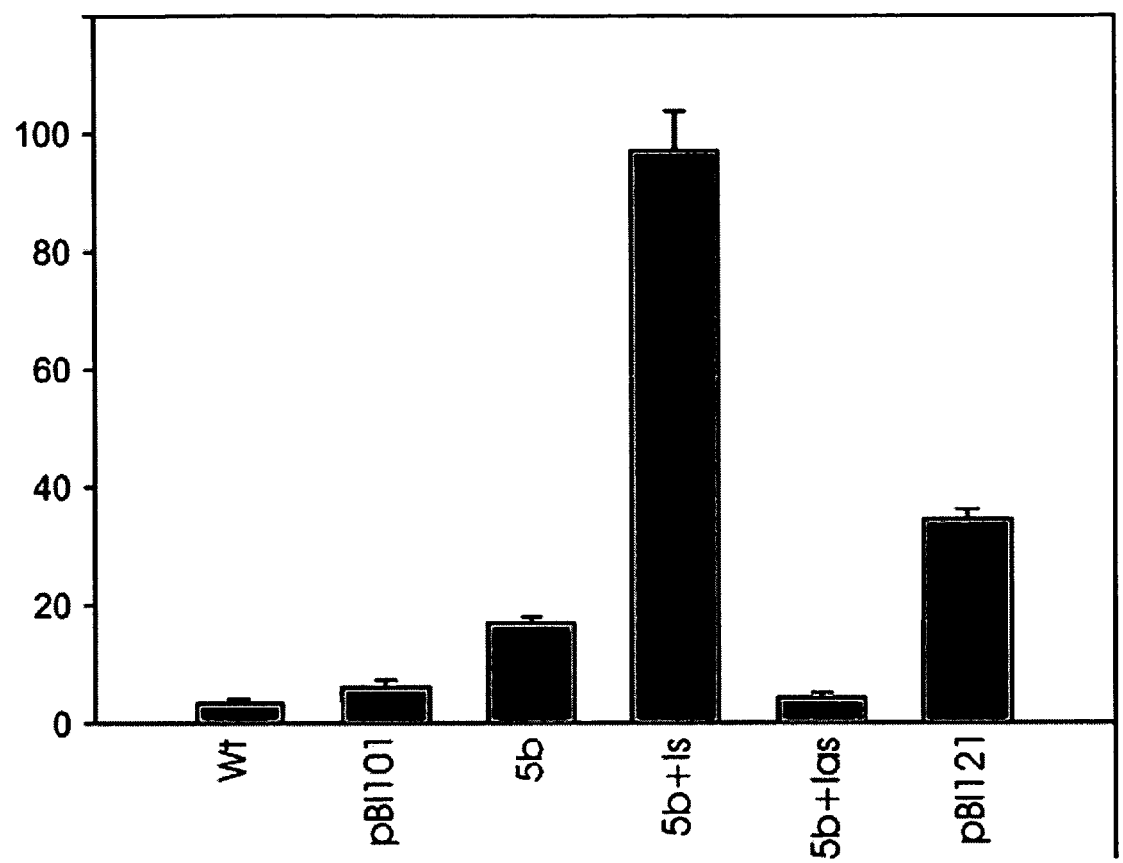

FIG. 5 shows a graph illustrating that the COX5c-2 leader intron increases expression from the unrelated COX5b-1 promoter. Specific GUS activity in extracts from plants transformed with a 609 bp COX5b-1 promoter fragment fused to gus (5b) or with a similar construct in which the COX5c-2 leader intron was inserted between the promoter and the gus coding region either in the sense (5b+Is) or antisense (5b+Ias) orientation was measured using the fluorogenic substrate MUG. GUS activity was also measured in extracts from non-transformed plants (wt) or from plants carrying the promoterless gus gene (pBI101) or the gus gene under the control of the CaMV 35S promoter (pBI121). Error bars represent SE of three independent measurements with one representative line from each construct. Similar results were obtained with different independent lines.

Figure 6:
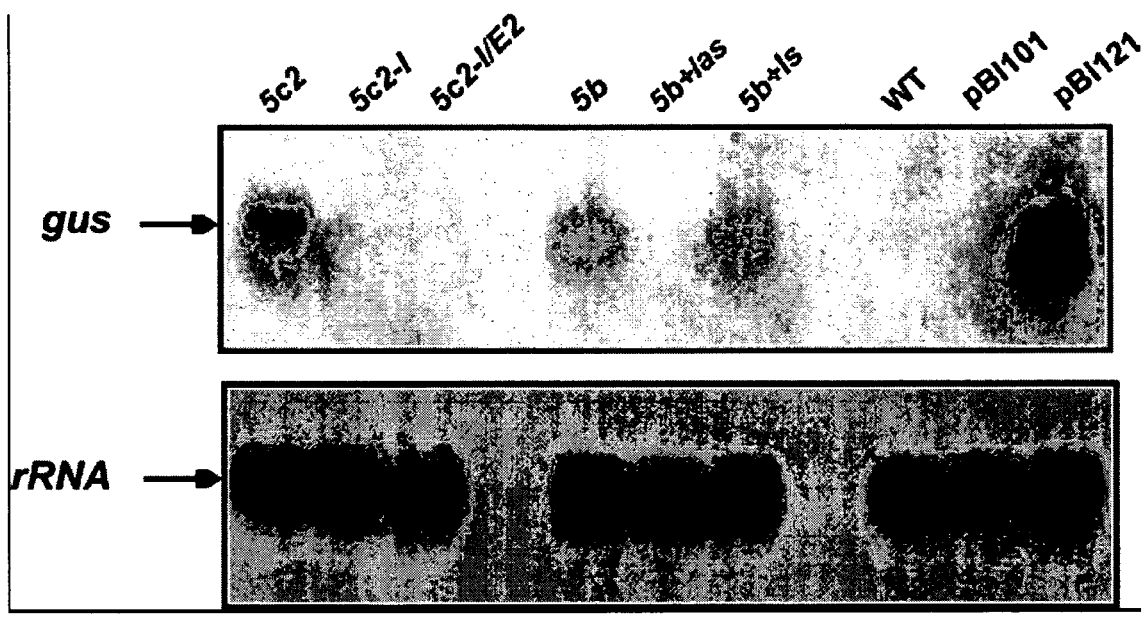

FIG. 6 shows a northern blot analysis of gus steady-state transcript levels using total RNA from plants transformed with constructs containing different portions of the COX5c-2 gene fused to gus. Total RNA (20 μg) from plants transformed with fragments containing COX5c-2 non-transcribed upstream regions and either the complete transcribed 5'-non-coding region (lane 1), only exon 1 sequences (lane 2), or the 5'-non-coding region without the intron (lane 3). Lanes 4, 5, and 6 contain RNA from plants transformed with a 609 bp COX5b-1 promoter fragment or the same fragment fused to the COX5c-2 leader intron in the antisense or sense orientation, respectively. Plants transformed with the promoterless gus gene (lane 7), non-transformed plants (lane 8), and plants transformed with the gus gene under the control of the CaMV 35S promoter (lane 9) were also analysed.

FIG. 7 shows DNA sequences isolated in the present invention:

SEQ No 1: COX5c-1 promoter;
SEQ No 2: COX5c-1 exon 1;
SEQ No 3 COX5c-1 intron;
SEQ No 4: COX5c-1 exon 2

FIG. 8 shows DNA sequences isolated in the present invention:

SEQ No 5: COX5c-2 promoter;
SEQ No 6: COX5c-2 exon 1;
SEQ No 7: COX5c-2 intron;
SEQ No 8: COX5c-2 exon 2

FIG. 9 shows DNA sequences isolated in the present invention:

SEQ No 9: COX5c-3 promoter;
SEQ No 10: COX5c-3 exon 2;
SEQ No 11: COX5c-3 intron;
SEQ No 12: COX5c-3 exon 2

DESCRIPTION OF THE PREFERRED EMBODIMENTS

Now referring in detail to the invention, the same refers to DNA molecules isolated from *Arabidopsis thaliana*, useful for the construction of expression cassettes and vectors in plants, their descendant, seeds, cells, wherein some of the sequences provided by the inventors enhance gene expression (introns, exons, promoters) in the whole plant, while the others produce such effect in a tissue-specific manner in the pollen.

The isolated DNA molecule can comprise SEQ No 3, SEQ No 7 or SEQ No 11, corresponding to COX5c-1, -2 and -3 introns respectively, or fragments, genetic variants or deletions thereof that conserve the capability of enhancing gene expression in plant cells.

The isolated DNA molecule can comprise SEQ No 1-2-3-4, SEQ No 5-6-7-8 or SEQ No 9-10-11-12, corresponding to COX5c-1, -2 and -3 gene promoter-exon 1-intron-exon 2, respectively, or fragments, genetic variants or deletions thereof that conserve the capability of enhancing gene expression in plant cells.

The isolated DNA molecule can comprise SEQ No 2-3-4, SEQ No 6-7-8 or SEQ No 10-11-12, corresponding to COX5c-1, -2 and -3 gene exon 1-intron-exon 2, respectively, or fragments, genetic variants or deletions thereof that conserve the capability of enhancing gene expression in plant cells.

The invention discloses the sequences located upstream of the start codon of the three *Arabidopsis thaliana* COX5c genes that drive tissue-specific expression in pollen, as well as the introns located in the 5'-non-coding region of all COX5c genes, and also that they are directly responsible for high gene expression levels observed in the tissues.

The isolated DNA molecule can comprise SEQ No 1-2-4, SEQ No 5-6-8 or SEQ No 9-10-12, corresponding to COX5c-1, -2 and -3 gene promoter-exon 1-exon 2, respectively, or fragments, genetic variants or deletions thereof that conserve the capability of enhancing tissue-specific gene expression in pollen.

Expression is observed throughout development, specially in vascular and meristematic tissues, and in pollen grains and siliques. The tissue-specific patterns of COX5c expression may be the consequence of responses to cell-specific factors or to the metabolic status of these tissues, which undergo constant cell proliferation.

It is noteworthy that removal of the leader intron produces a pronounced decrease in expression levels for both genes, making reporter gene activity barely detectable, except in pollen grains.

*Arabidopsis thaliana* Heyhn. ecotype Columbia (Col-0) was purchased from Lehle Seeds (Tucson, Ariz.). Plants were grown on soil in a growth chamber at 22-24° C. under long-day photoperiods (16 h of illumination by a mixture of cool-white and GroLux fluorescent lamps) at an intensity of approximately 200 μE $m^{-2}$ $s^{-1}$. Plants used for the different treatments were grown in Petri dishes containing 0.5× Murashige and Skoog medium and 0.8% agar. The dishes were kept at 4° C. for 2 d and then transferred to growth chamber conditions and kept in complete darkness for 7 d.

Isolation of genomic clones was performed as follows: *Arabidopsis* EST clones encoding COX5c-1 and COX5c-2 (clones 245H10T7, accession no. N97140, and 248L23T7, accession no. AA713295) were obtained from ABRC. For the isolation of genomic clones, a mixture of these cDNAs was used to screen 1×10⁵ pfu from an *Arabidopsis* genomic library (Voytas et al., 1990). Phage DNA was transferred to Hybond-N® and, after overnight hybridization; filters were washed and exposed to X-ray films. Positive clones were purified through successive rounds of plating and hybridization. Isolated phage DNA from purified clones was characterized by restriction analysis and hybridization. A 1.8 kbp EcoRI fragment from COX5c-1 and a 3.2 kbp EcoRI/NheI fragment from COX5c-2, comprising the entire transcribed region and upstream sequences, were subcloned into pBluescript SK⁻ digested with EcoRI or EcoRI and XbaI, respectively. Positive clones were checked by partial sequencing and named VCAT1 and VCAT2.

In order to analyse transgenic plants, total RNA was isolated as described by Carpenter and Simon (1998). For northern blot analysis, specific amounts of RNA were electrophoresed through 1.5% (w/v) agarose/6% formaldehyde gels. The integrity of the RNA and equality of RNA loading were verified by ethidium bromide staining. RNA was transferred to Hybond-N® nylon membranes (Amersham Corporation) and hybridized overnight at 68° C. to a ³²P-labelled cDNA probe, comprising the entire GUS coding region isolated from vector pBI101.3, in buffer containing 6×SSC, 0.1% (w/v) polyvinylpyrrolidone, 0.1% (w/v) BSA, 0.1% (w/v) Ficoll, 0.2% (w/v) SDS, and 10% (w/v) polyethylene glycol 8000. Filters were washed with 2×SSC plus 0.1% (w/v) SDS at 68° C. (4 times, 15 mm each), 0.1×SSC plus 0.1% (w/v) SDS at 37° C. for 15 mm, dried, and exposed to Kodak® BioMax™ MS films. To check the amount of total RNA loaded in each lane, filters were then re-probed with a 25S rRNA from *Vicia faba* under similar conditions as those described above, except that hybridization was performed at 62° C. and the wash with 0.1×SSC was omitted.

Reporter gene constructs and plant transformation were performed as follows: a 1.3 kbp BglII/SalI fragment, comprising sequences upstream of the ATG initiation codon (i.e. exon 1, the intron and part of exon 2, plus non-transcribed upstream sequences) from COX5c-1, was amplified from clone VCAT1 using oligonucleotide COXC32: 5'-GGC AGATCTCTCTTCTTTCTTCTTCTC-3' (SEQ ID NO:13) (BglII site underlined) and universal primer –40 and cloned in plasmid pBI101.3 digested with BamHI and SalI. A similar construct for COX5c-2 was made by amplifying a 2.2 kbp fragment from VCAT2 with primers COXC41: 5'-GCG TCTAGATTCTTCTCAACCTAGCAC-3' (SEQ ID NO:14) (XbaI site underlined) and –40 and cloning in pBI101.3 digested with XbaI and HindIII. Constructs containing exon 1 and upstream sequences were obtained in a similar way by amplification with either COXC33: 5'-GGC GGATCCCAAGTCGGAGTGTGGAGG-3' (SEQ ID NO:15) (COX5c-1) or COXC42: 5'-GGC GGATCCCGAGTCAGATTGTGTAGA-3' (SEQ ID NO:16) (COX5c-2), followed by cloning in the SalII/BamHI or HindIII/BamHI sites of pBI101.3, respectively. A construct containing the entire COX5c-2 5'-non-coding region without the intron was obtained by amplification with primers COXC45: 5'-GCGTCTAGATTCTTCTCAACCGAGTCAGATTG TGTAGA-3' (SEQ ID NO:17) and –40 followed by cloning into the XbaI and HindIII sites of pBI101.3. To test the effect of the intron on an exogenous promoter, the COX5c-2 intron and transcribed 5'-non-coding sequences were amplified with primers COXC44: 5'-GGCTCTAGAGTTTTCGTCGT-GAGCTTC-3' (SEQ ID NO:18) and COXC41 and cloned in both orientations into the XbaI site of a construct containing a 609 bp promoter fragment from the COX5b-1 gene fused to gus (Welchen et al., 2004). In this way, the intron was placed between the COX5b-1 promoter and the gus coding region. The different constructs were introduced into *Agrobacterium tumefaciens* strain GV2260, and transformed bacteria were used to obtain transgenic *Arabidopsis* plants by the floral dip procedure (Clough and Bent, 1998). Transformed plants were selected on the basis of kanamycin resistance and positive PCR carried out on genomic DNA with primers specific for COX5c-1 or -2 and the gus-specific primer 5'-TTGGGGTTTCTACAGGAC-3' (SEQ ID NO:19). Five to ten independent lines (depending on the construct) were further reproduced and homozygous T3 and T4 plants were used to analyse gus expression. Plants transformed with pBI101.3 or pBI121 were obtained in a similar way and used as negative or positive controls of expression, respectively.

β-glucuronidase (GUS) activity of transgenic plants was analysed by histochemical staining using the chromogenic substrate 5-bromo-4-chloro-3-indolyl-β-D-glucuronic acid (X-gluc) as described by Hull and Devic (1995). Whole plants or separated organs were immersed in a 1 mM X-gluc solution in 100 mM sodium phosphate, pH 7.0, and 0.1% Triton X-100 and, after applying vacuum for 5 min, they were incubated at 37° C. until satisfactory staining was observed. Tissues were cleared by immersing them in 70% ethanol.

Specific GUS activity in protein extracts was measured using the fluorogenic substrate 4-methylumbelliferyl β-D-glucuronide (MUG) essentially as described by Jefferson et al. (1987). Total protein extracts were prepared by grinding the tissues in extraction buffer (50 mM sodium phosphate, pH 7.0, 10 mM EDTA, 10 mM β-mercaptoethanol) containing 0.1% (w/v) SDS and 1% Triton X-100, followed by centrifugation at 13 000 g for 10 min. GUS activity in supernatants was measured in extraction buffer containing 1 mM MUG and 20% methanol. Reactions were stopped with 0.2 M $Na_2CO_3$ and the amount of 4-methylumbelliferone was calculated by relating relative fluorescence units with those of a standard of known concentration. The protein concentration of extracts was determined as described by Kruger (1996).

The involvement of regions located upstream of the translation start site in the expression of two *Arabidopsis thaliana* nuclear COX5c genes encoding subunit 5c of mitochondrial cytochrome c oxidase has been analysed. It was observed that these regions, which include a leader intron, direct the tissue-specific expression of the gus reporter gene, mainly in root and shoot meristems, actively growing tissues and vascular strands. It is important to remark that based in the similarity of sequences and origin of COX5c genes, it is expected that the results obtained for COX5c-1 and COX5c-2 would be the same to be obtained for COX5c-3 or any fragment thereof.

Expression was also observed in flowers, specifically localized in anthers, stigma, and the receptacle, and in developing seeds.

GUS activity measurements in protein extracts from transformed plants shows that expression levels are higher than those observed with the constitutive CaMV 35S promoter.

Removal of the leader intron produced a significant decrease in expression to values only slightly higher than those observed with a promoterless gus gene.

Histochemical staining of plants transformed with the intronless construct revealed expression only in pollen, suggesting that regulatory elements capable of directing pollen-specific expression are present upstream of the intron.

The COX5c-2 intron also increased GUS expression levels when fused in the correct orientation with the promoter of the unrelated COX5b-1 gene. It is noteworthy that the invention can contain one of the COX5c introns fused with a variety of promoters, such as Hahb-4 promoter sequences of Patent No. PCT/US 03/13770 which is incorporated as a reference. The effects obtained by the expression of heterologous genes in plants depends on the kinetic of their expression and the reached final levels of the expression. Thus the sequences of the present invention may be applied in the transformation of plants. Particularly in connection to a transformation to improve tolerance to salinity and drought induced by Hahb-4, the expression of Hahb-4, enhanced by the inventive sequences, results into higher survival levels of the transformed plant as well as a faster response of the plant to resist the environmental stresses.

Comparison of GUS activity values with the transcript levels suggests that the intron also increases translation efficiency of the corresponding mRNA. The results obtained point to an essential role of the intron present in the 5'-non-coding region of all known COX5c genes in directing the expression of these genes in plants.

The invention may be better understood with reference to the following examples which are not limitative or restrictive of the scope of protection. On the contrary, it must be clearly understood that many other embodiments, modifications and alterations equivalent to the elements of the invention may be suggested by persons skilled in the art after reading the present description, without departing from the spirit of the present invention and/or the scope of the appended claims.

EXAMPLES

Example 1

COX5c Related Sequences in the *Arabidopsis* Genome

Figure 1:
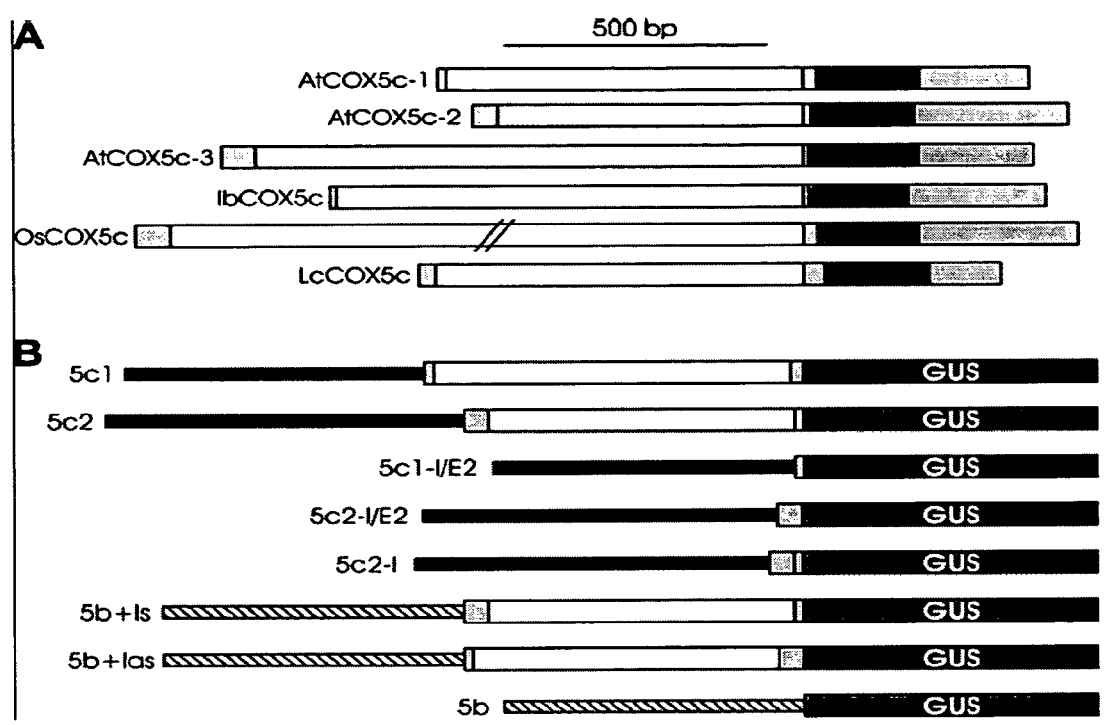
FIG. 1 shows COX5c genes schemes (A, upper panel) and (B, lower panel), which contain an intron within the 5'-non-coding region.

A search for COX5c coding regions in the *Arabidopsis* genome using sunflower COX5c protein sequences (Curi et al., 2002) and the program TBLASTN revealed the existence of four genomic regions from which proteins with COX5c-related sequences could be deduced. For three of them (At2g47380, At3g62400, and At5g61310) mRNA sequences are also deposited in data banks, indicating that they are expressed. The fourth region, located in chromosome 5, encodes a protein more distantly related for which no transcripts have been detected, suggesting that it may be a pseudogene. Accordingly, the genes present in chromosomes 2, 3 and 5 have arbitrarily been named COX5c-1, COX5c-2, and COX5c-3, respectively. Upon comparing the corresponding genomic and cDNA sequences, it becomes evident that the three *Arabidopsis* COX5c genes contain a single intron located within the 5'-non-coding region, at variable distances with respect to the ATG start codon (FIG. 1A). An intron in the same location is also present in the other COX5c genes for which sequences are available, the single genes from rice (*Oryza sativa*; BAC clone accession number AB027123), sweet potato (*Ipomoea batatas*; Nakagawa et al., 1993), and *Lotus corniculatus* (BAC clone accession number AP006137).

Example 2

Sequences Upstream of the Translation Start Site of COX5c-1 and COX5c-2 Promote High-Level Expression of a Reporter Gene in Specific Cell-Types Two *Arabidopsis thaliana* clones containing the COX5c-1 and -2 genes and additional genomic regions were isolated by direct screening of a library using a mixture of ESTs derived from these genes. Subclones of these lambda clones were used to amplify fragments containing sequences located upstream of the translation start site which were introduced in vector pBI101.3 in front of the gus coding region (FIG. 1B). These constructs (pBI5c1 and pBI5c2 for COX5c-1 and -2, respectively) were introduced into *Arabidopsis* by *Agrobacterium*-mediated transformation. An initial screening of kanamycin-resistant lines was carried out by histochemistry to define expression characteristics common to most of them. Plants from at least five independent representative transgenic lines carrying each construct were then analysed in detail. The results were essentially the same for all plants analysed, carrying either pBI5c1 or pBI5c2.

Seedlings grown on Petri dishes on MS medium showed strong staining along roots and hypocotyls, while activity in cotyledons was detected only in plants older than 3 d post-germination (FIG. 2A, B). Activity in roots was progressively localized to the vascular cylinder and the root meristem upon growth (FIG. 2B). After 15 d, strong expression was also detected in developing secondary roots (FIG. 2C). In hypocotyls, activity was also progressively localized to vascular tissues upon development (FIG. 2D). Cotyledons displayed GUS activity in the lamina and especially in vascular tissues (FIG. 2D, E). A similar expression pattern was evident in developing leaves (FIG. 2D, E). Strong activity was also observed in the shoot apical meristem (FIG. 2F).

Adult (45-d-old) plants grown on soil displayed activity in roots, leaves, and flowers. Expression in roots was similar to that described for younger plants. In leaves, vascular tissues and, to a lesser extent, mesophyll tissues were stained (FIG. 2G). In flowers, strong expression was detected in anthers, especially in reproductive tissues and pollen grains when these were formed (FIG. 2H, I). Activity was also detected in the stigma, receptacle, and petal and sepal veins, and in siliques and developing seeds (FIG. 2I, J).

To estimate the relative expression levels produced by both constructs, fluorometric assays of GUS activity in protein extracts from transformed 20-d-old plants were performed. Plants transformed with pBI5c1 and pBI5c2 displayed activities of 35 000 pmol min$^{-1}$ mg$^{-1}$ and 66 000 pmol min$^{-1}$ mg$^{-1}$, respectively. These values are even higher than those observed with plants transformed with pBI121 (i.e. the gus gene under the control of the strong constitutive CaMV 35S promoter), 18 000 pmol min$^{-1}$ mg$^{-1}$, indicating that the sequences contained within the constructs direct high-level expression. Activity measurements using extracts from different organs indicated that highest expression was attained in leaves followed by flowers, siliques, and roots (not shown).

Example 3

Removal of the Leader Intron Originates Plants with Pollen-Specific Expression

The presence of a conserved intron in the leader region led to the investigation of its role in expression of COX5c genes. Seedlings of plants transformed with constructs in which the respective leader introns from COX5c-1 or COX5c-2 and downstream sequences were removed (5c1-I/E2 and 5c2-I/E2 in FIG. 1B) showed no GUS activity when analysed by histochemical staining (FIG. 2K). Analysis of adult plants revealed the presence of GUS activity only in pollen grains (FIG. 2M, N), while no staining was evident in leaves, siliques, or flower organs other than anthers (FIG. 2L-O). Similar results were observed for both genes under study, indicating that the leader intron is essential to direct high-level expression throughout the plant. Indeed, activity in pollen was also reduced in these plants, since longer incubation times were required to reach similar staining: 18 h with plants transformed with the intronless constructs versus 3-5 h with plants transformed with the entire fragments. The levels of GUS activity present in protein extracts from plants transformed with the intronless constructs were extremely low: 800 and 1400 pmol min$^{-1}$ mg$^{-1}$, respectively, for COX5c-1 and COX5c-2, that is 40-50 times lower than those observed when the intron was present.

Zabaleta et al. (1998) have studied the promoter regions involved in pollen/anther expression of three genes that encode components of the NADH dehydrogenase (Complex I). Within these regions, they have identified conserved GT-rich elements similar to those found in other genes expressed in pollen. They have postulated that these motifs are involved in the co-ordinated expression of the three genes. Analysis of the promoter regions of both COX5c genes showed the presence of GT-rich elements (TGTGGTT and TGTGTTG for COX5c-1 and -2), located at −208 and −210, respectively, from the putative transcription start site. The first of these elements is identical to those observed in one of the Complex I genes and in the tomato LAT52 and LAT56 genes, specifically expressed in pollen (Twell et al., 1991). Both genes also possess two close copies of site II elements (TGGGCC/T), located at −109/−90 and −84/−71, respectively, known to be present in genes preferentially expressed in cycling cells (Kosugi et al., 1995; Trémousaygue et al., 2003). The functional significance of these sequences must be assessed by mutagenesis experiments.

Example 4

Untranslated Exon Sequences Influence Gus Expression

Comparison of GUS activities with the respective transcript levels indicate that COX5c 5'-non-coding sequences also increase translation efficiency. This observation could be made with constructs that possess the COX5c leader introns, but not with those that only carry non-coding exon sequences, due to the low expression levels produced by the latter. It should be emphasized that the context of the start codon, which could affect translation efficiency, is the same in all constructs analysed, since they use the ATG provided by the pBI101.3 vector which is placed several nucleotides downstream of the cloning sites. The differences in translation efficiency are then produced by the intron itself or by the presence of translational enhancers in the 5'-non-coding region. So far, similarities with other known translational enhancers (Yamamoto et al., 1995; Dickey et al., 1998) within COX5c untranslated regions have not been observed.

The effect of 5' untranslated exon regions on expression was also analysed. For this purpose, plants transformed with a construct in which the COX5c-2 leader intron was removed, but the promoter and 5'-non-coding sequences from exons 1 and 2 were conserved (5c2-I in FIG. 1B), were used. These plants showed considerably lower GUS activity levels than plants carrying the construct with the intron (FIG. 3). They consistently showed, however, slightly higher activities than plants bearing only the promoter and exon 1 fused to gus (FIG. 3, inset). The different expression produced by the inclusion of exon 2 non-coding sequences was also observed by histochemical staining. Indeed, activity, although low, was detected in cotyledon veins and tips and also in leaf veins, trichomes, and hydathodes (FIG. 2P-R). In reproductive tissues, expression was only detected in pollen, as with the construct in which the intron and exon 2 were removed (FIG. 2S, T). These results, on one side, confirm the importance of the leader intron in determining high level expression and, on the other side, indicate that non-coding exon sequences, though slightly, also influence gene expression.

Example 5

The COX5c-2 Leader Intron and Adjacent Regions Increase the Expression of an Unrelated Promoter The effect of the inclusion of the COX5c-2 intron between the promoter of an unrelated gene and the gus coding region was also tested. For this purpose, a region covering the entire intron and surrounding untranslated transcribed sequences from COX5c-2 was inserted between the promoter of the *Arabidopsis* gene COX5b-1 and the gus coding region, either in the sense or antisense orientation (5b+Is and 5b+Ias, respectively, in FIG. 1B). The portion of the COX5b-1 promoter used (−1 to −609 respective to the translation start site) directs relatively low expression localized in meristems, root, and cotyledon vascular tissues, the leaf central vein, and in anthers (Welchen et al., 2004). Inclusion of the COX5c-2 intron in the correct orientation resulted in considerably higher expression levels throughout the plant, in a pattern similar to those observed with the COX5c-1 and COX5c-2 promoter plus intron fragments (FIG. 4). As a consequence, GUS activity was extended from vascular tissues and anthers, as observed in plants bearing only the COX5b-1 promoter fragment without the intron (FIG. 4A, B, G, J, M, N), to the lamina of cotyledons and leaves (FIG. 4D, E, H, K) and to petals and siliques (FIG. 4O, P). GUS activity measurements in protein extracts from transformed plants indicated that the intron produces a 6-fold increase in expression levels from the COX5b-1 promoter (FIG. 5).

When the intron was placed in the same location, but in reverse orientation, GUS activity was not detected in any tissue or developmental stage by either the histochemical (FIG. 4C, F, I, L) or the fluorometric method (FIG. 5). It is logical to assume that intron splicing does not take place when the intron is present in the reverse orientation. The presence of a large non-coding sequence in the 5 region of the transcript may either affect its stability or its translation efficiency. Six spurious ATG codons are introduced when the intron is placed in the reverse orientation, thus probably affecting the recognition of the correct start codon by the translation machinery. In addition, it is well-known that transcripts with premature termination stop codons in phase with a start codon are degraded by a process termed nonsense-mediated mRNA decay (Baker and Parker, 2004).

Example 6

COX5c Leader Introns and Adjacent Regions Increase Translation Efficiency

The increase in expression promoted by the presence of the intron was also observed when analysing transcript levels of the gus gene under the control of the respective fragments from COX5c-1 and COX5c-2. FIG. 6 shows a northern hybridization using a gus probe and total RNA from plants carrying different portions of the COX5c-2 gene. While no or extremely faint signals were obtained in northern blots with total RNA from plants carrying the intronless constructs (FIG. 6, lanes 2, 3), a distinct band was visible in the sample from plants bearing the construct with the COX5c-2 intron (FIG. 6, lane 1). Transcript levels in these plants, however, were considerably lower than those observed in plants transformed with the T-DNA region of plasmid pBI121, which contains the gus gene under the control of the CaMV 35S promoter (FIG. 6, lane 9). Densitometric analysis of the respective bands, compared with the signals obtained with the rRNA probe, indicated that gus transcript levels are seven times higher in plants transformed with the CaMV 35S promoter fusion. Since plants transformed with the entire COX5c fragments showed 3.5 times higher GUS activities than the latter (see above), this suggests that transcripts containing COX5c 5'-non-coding sequences are more efficiently translated, producing a 25-fold increase in the protein/transcript ratio. Although protein levels were not directly quantified, it can be assumed that enzyme activity measurements constitute an appropriate estimation, since all constructs must produce proteins with the same amino acid sequence. An effect of the intron on translation could also be observed when analysing transcript levels of plants transformed with the COX5b-1 gene promoter with or without the COX5c-2 intron (FIG. 6, lanes 4, 6). In this case, the increase in transcript levels promoted by the presence of the intron was very low compared with the 6-fold increase in GUS activity observed in plants with the intron in the correct orientation. On the other hand, plants with the intron in the antisense orientation showed undetectable levels of gus transcripts (FIG. 6, lane 5). Although this may be due to a lower transcription efficiency, a more likely explanation is that the unspliced RNA is rapidly degraded.

While preferred embodiments of the present invention have been illustrated and described, it will be obvious to those skilled in the art that various changes and modifications may be made therein without departing from the scope of the invention as defined in the appended claims.

REFERENCES

Baker K E, Parker R. 2004. Nonsense-mediated mRNA decay: terminating erroneous gene expression. *Current Opinion in Cell Biology* 16, 293-299.

Bolle C, Hermann R G, Oelmüller R. 1996. Intron sequences are involved in the plastid and light-dependent expression of the spinach PsaD gene. *The Plant Journal* 10, 919-924.

Callis J, Fromm M, Walbot V. 1987. Introns increase gene expression in cultured maize cells. *Genes and Development* 1, 1183-1200.

Grossman, L, Lomax M. 1997. Nuclear genes for cytochrome c oxidase. *Biochimica et Biophysica acta* 1352, 174-192.

Carpenter C D, Simon A E. 1998. Preparation of RNA. In: Martinez-Zapater J, Salinas J, eds. *Methods in molecular biology*, Vol. 82. *Arabidopsis protocols*. Totowa, N.J.: Humana Press Inc, 85-89.

Christensen A H, Sharrock R A, Quail P H. 1992. Maize polyubiquitin genes: structure, thermal perturbation of expression and transcript splicing, and promoter activity following transfer to protoplasts by electroporation. *Plant Molecular Biology* 18, 675-689.

Clough S J, Bent A F. 1998. Floral dip: a simplified method for *Agrobacterium*-mediated transformation of *Arabidopsis thaliana*. *The Plant Journal* 16, 735-743.

Curi G C, Chan R L, Gonzalez D H. 2002. Genes encoding cytochrome c oxidase subunit 5c from sunflower (*Helianthus annuus* L.) are regulated by nitrate and oxygen availability. *Plant Science* 163, 897-905.

Curi G C, Welchen E, Chan R L, Gonzalez D H. 2003. Nuclear and mitochondrial genes encoding cytochrome c oxidase subunits respond differently to the same metabolic factors. *Plant Physiology and Biochemistry* 41, 689-693.

Dickey L F, Petracek M E, Nguyen T T, Hansen E R, Thompson W F. 1998. Light regulation of Fed-1 mRNA requires an element in the 5' untranslated region and correlates with differential polyribosome association. *The Plant Cell* 10, 475-484.

Elorza A, León G, Gómez I, Mouras A, Holuigue L, Araya A, Jordana X. 2004. Nuclear SDH2-1 and SDH2-2 genes, encoding the iron-sulfur subunit of mitochondrial complex II in *Arabidopsis*, have distinct cell-specific expression patterns and promoter activities. *Plant Physiology* 136, 4072-4087.

Felitti S A, Chan R L, Gago G, Valle E M, Gonzalez D H. 1997. Expression of sunflower cytochrome c mRNA is tissue-specific and controlled by nitrate and light. *Physiologia Plantarum* 99, 342-347.

Gidekel M, Jimenez B, Herrera-Estrella L. 1996. The first intron of the *Arabidopsis thaliana* gene coding for elomgation factor 1 beta contains an enhancer-like element. *Gene* 170, 201-206.

Hamanaka S, Ohtsu K, Kadowaki K, Nakazono M, Hirai A. 1999. Identification of cDNA encoding cytochrome c oxidase subunit 5c (COX5c) from rice: comparison of its expression with nuclear-encoded and mitochondrial-encoded COX genes. *Genes and Genetic Systems* 74, 71-75.

Heiser V, Brennicke A, Grohmann L. 1996. The plant mitochondrial 22 kDa (PSST) subunit of respiratory chain complex I is encoded by a nuclear gene with enhanced transcript levels in flowers. *Plant Molecular Biology* 31, 1195-1204.

Huang J, Struck F, Matzinger D F, Levings III C S. 1994. Flower-enhanced expression of a nuclear-encoded mitochondrial respiratory protein is associated with changes in mitochondrion number. *The Plant Cell* 6, 439-448.

Hull G A, Devic M. 1995. The beta-glucuronidase (gus) reporter gene system. Gene fusions; spectrophotometric, fluorometric, and histochemical detection. In: Jones H, ed. *Methods in plant molecular biology*, Vol. 49. *Plant gene transfer and expression protocols*. Totowa, N.J.: Humana Press Inc, 125-141.

Jänsch L, Kruft V, Schmitz U K, Braun H-P. 1996. New insights into the composition, molecular mass and stoichiometry of the protein complexes of plant mitochondria. *The Plant Journal* 9, 357-368.

Jefferson R A, Kavanagh T A, Bevan M W. 1987. GUS fusions: β-glucuronidase as a sensitive and versatile gene fusion marker in higher plants. *EMBO Journal* 20, 3901-3907.

Jeon J-S, Lee S, Jung K-H, Jun S-H, Kim C, An G. 2000. Tissue preferential expression of a rice α-tubulin gene, OstubA1, mediated by the first intron. *Plant Physiology* 123, 1005-1014.

Kadowaki K, Kubo N, Ozawa K, Hirai A. 1996. Targeting presequence acquisition after mitochondrial gene transfer to the nucleus occurs by duplication of existing targeting signal. *EMBO Journal* 15, 6652-6661.

Kosugi S, Suzuka I, Ohashi Y. 1995. Two of three promoter elements identified in a rice gene for proliferating cell nuclear antigen are essential for meristematic tissue-specific expression. *The Plant Journal* 7, 877-886.

Landschütze V, Müller-Röber B, Willmitzer L. 1995. Mitochondrial citrate synthase from potato: predominant expression in mature leaves and young flower buds. *Planta* 196, 756-764.

Le Hir H, Nott A, Moore M J. 2003. How introns influence and enhance eukaryotic gene expression. *Trends in Biochemical Sciences* 28, 215-220.

Zdravko J. Lorkovî c, Dominika A. Wieczorek Kirk, Mark H. L. Lambermon and Witold Filipowicz. 2000. Pre-mRNA splicing in higher plants. *Trends in plant science Reviews*. 5(4), 160-167.

Mascarenhas. D.; Mettler, I. J.; Pierce, D. A. and Lowe, H. W. (1990). Intron-mediated enhancement of heterologous gene expression in maize. Plant Mol. Biol. 15:913-920.

McElroy D, Zhang J, Cao J, Wu R. 1991. Isolation of an efficient actin promoter for use in rice transformation. *The Plant Cell* 2, 163-171.

Millar A H, Eubel H, Jansch L, Kruft V, Heazlewood J L, Braun H-P. 2004. Mitochondrial cytochrome c oxidase and succinate dehydrogenase complexes contain plant specific subunits. *Plant Molecular Biology* 56, 77-90.

Morello L, Bardini M, Sala F, Breviario D. 2002. A long leader intron of the Ostub16 rice β-tubulin gene is required for high-level gene expression and can autonomously promote transcription both in vivo and in vitro. *The Plant Journal* 29, 33-44.

Mun J H, Lee S Y, Yu H J, Jeong Y M, Shin M Y, Kim H, Lee I, Kim S G. 2002. Petunia actin-depolymerizing factor is mainly accumulated in vascular tissue and its gene expression is enhanced by the first intron. *Gene* 292, 233-243.

Nakagawa T, Maeshima M, Muto H, Kajiura H, Hattori H, Asahi T. 1987. Separation, amino-terminal sequence and cell-free synthesis of the smallest subunit of sweet potato cytochrome c oxidase. *European Journal of Biochemistry* 165, 303-307.

Nakagawa T, Maeshima M, Nakamura K, Asahi T. 1990. Molecular cloning of a cDNA for the smallest nuclear-encoded subunit of sweet potato cytochrome c oxidase. Analysis with the cDNA of the structure and import into mitochondria of the subunit. *European Journal of Biochemistry* 191, 557-561.

Nakagawa T, Maeshima M, Nakamura K, Asahi T. 1993. The nuclear gene for subunit Vc of sweet potato cytochrome c oxidase. *Plant and Cell Physiology* 34, 621-626.

Norris S R, Meyer S E, Callis J. 1993. The intron of *Arabidopsis thaliana* polyubiquitin genes is conserved in location and is a quantitative determinant of chimeric gene expression. *Plant Molecular Biology* 21, 895-906.

Nott A, Le Hir H, Moore M J. 2004. Splicing enhances translation in mammalian cells: an additional function of the exon junction complex. *Genes and Development* 18, 210-222.

Ohtsu K, Nakazono M, Tsutsumi N, Hirai A. 2001. Characterization and expression of the genes for cytochrome c oxidase subunit VIb (COX6b) from rice and *Arabidopsis thaliana*. *Gene* 264, 233-239.

Plesse B, Criqui M C, Durr A, Parmentier Y, Fleck J, Genschik P. 2001. Effects of the polyubiquitin gene Ubi.U4 leader intron and first ubiquitin monomer on reporter gene expression in *Nicotiana tabacum*. *Plant Molecular Biology* 45, 655-667.

Ribichich K, Tioni M F, Chan R L, Gonzalez D H. 2001. Cell-type specific expression of plant cytochrome c mRNA in developing flowers and roots. *Plant Physiology* 125, 1603-1610.

Rose A B. 2004. The effect of intron location on intron-mediated enhancement of gene expression in *Arabidopsis*. *The Plant Journal* 40, 744-751.

Rose A B, Last R L. 1997. Introns act post-transcriptionally to increase expression of the *Arabidopsis thaliana* tryptophan pathway gene PAT1. The Plant Journal 11, 455-464.

Kruger N. 1996. The Bradford Method for Protein Quantitation. In: John Walker editor. The Protein Protocols. Humana Press 4, 15-20.

Simpson, G. G. and Filipowicz, W. 1996. Splicing of precursors to mRNA in higher plants: mechanism, regulation and sub-nuclear organisation of the spliceosomal machinery. *Plant Molecular Biology*. 32, 1-41.

Smart C, Monéger F, Leaver C J. 1994. Cell-specific regulation of gene expression in mitochondria during anther development in sunflower. *The Plant Cell* 6, 811-825.

Trémousaygue D, Garnier L, Bardet C, Dabos P, Hervé C, Lescure B. 2003. Internal telomeric repeats and "TCP-domain" protein binding sites co-operate to regulate gene expression in *Arabidopsis thaliana* cycling cells. *The Plant Journal* 33, 957-966.

Twell D, Yamaguchi J, Wing R, Ushiba J, McCormick S. 1991. Promoter analysis of genes that are coordinately expressed during pollen development reveals pollen-specific enhancer sequences and shared regulatory elements. *Genes and Development* 5, 496-507.

Voytas D F, Konieczny A, Cummings M P, Ausubel F M. 1990. The structure, distribution and evolution of the Ta1 retrotransposable element family of *Arabidopsis thaliana*. *Genetics* 126, 713-721.

Welchen E, Chan R L, Gonzalez D H. 2002. Metabolic regulation of genes encoding cytochrome c and cytochrome c oxidase subunit Vb in *Arabidopsis*. *Plant Cell and Environment* 25, 1605-1615.

Welchen E, Chan R L, Gonzalez D H. 2004. The promoter of the *Arabidopsis* nuclear gene COX5b-1, encoding subunit 5b of the mitochondrial cytochrome c oxidase, directs tissue-specific expression by a combination of positive and negative regulatory elements. *Journal of Experimental Botany* 55, 1997-2004.

Wiegand H L, Lu S, Cullen B R. 2003. Exon junction complexes mediate the enhancing effect of splicing on mRNA expression. *Proceedings of the National Academy of Sciences of the USA* 100, 11327-11332.

Xu Y, Yu H, Hall T C. 1994. Rice triosephosphate isomerase gene 5' sequence directs β-glucuronidase activity in transgenic tobacco but requires an intron for expression in rice. *Plant Physiology* 106, 459-467.

Yamamoto Y Y, Tsuji H, Obokata J. 1995. 5' Leader of a photosystem I gene in *Nicotiana sylvestris*, psaDb, contains a translational enhancer. *The Journal of Biological Chemistry* 270, 12466-12470.

Zabaleta E, Heiser V, Grohmann L, Brennicke A. 1998. Promoters of nuclear-encoded respiratory chain complex I genes from *Arabidopsis thaliana* contain a region essential for anther/pollen-specific expression. *The Plant Journal* 15, 49-59.

The invention claimed is:

1. An isolated DNA molecule comprising SEQ ID NO:3, wherein SEQ ID NO:3 is operably linked to a promoter that is heterologous thereto, and a coding sequence.

2. An expression cassette comprising a promoter sequence linked to SEQ ID NO:3, which is operably linked to a coding sequence, wherein said promoter sequence is heterologous to SEQ ID NO:3 and wherein said SEQ ID NO:3 increases the expression level of the coding sequence in plant cells compared to plant cells transformed with an expression cassette comprising the promoter sequence operably linked to the coding sequence and lacking the polynucleotide of SEQ ID NO:3.

3. The expression cassette of claim 2, wherein said expression level is increased in all tissues of an adult plant compared to an adult plant transformed with an expression cassette comprising the promoter sequence operably linked to the coding sequence and lacking the polynucleotide of SEQ ID NO:3.

4. The expression cassette of claim 2, wherein said coding sequence is heterologous to said SEQ ID NO:3.

5. A plant cell transformed with an expression cassette comprising a promoter sequence linked to SEQ ID NO:3, which is operably linked to a coding sequence, wherein said promoter sequence is heterologous to SEQ ID NO:3 and wherein said SEQ ID NO:3 increases the expression level of the coding sequence in the plant cell compared to a plant cell transformed with an expression cassette comprising the promoter sequence operably linked to the coding sequence and lacking the polynucleotide of SEQ ID NO:3.

6. The plant cell of claim 5, wherein the expression cassette is stably integrated into the plant cell genome.

7. The plant cell of claim 5, wherein said coding sequence is heterologous to said SEQ ID NO:3.

8. A transgenic plant transformed with an expression cassette comprising a promoter sequence linked to SEQ ID NO:3, which is operably linked to a coding sequence, wherein said promoter sequence is heterologous to SEQ ID NO:3; and wherein said SEQ ID NO:3 increases the expression level of the coding sequence in the transgenic plant compared to a transgenic plant transformed with an expression cassette comprising the promoter sequence operably linked to the coding sequence and lacking the polynucleotide of SEQ ID NO:3.

9. The transgenic plant of claim 8, wherein said coding sequence is heterologous to said SEQ ID NO:3.

10. The transgenic plant of claim 8, wherein said plant is selected from the group consisting of monocot and dicot plants.

11. A transgenic seed transformed with an expression cassette comprising a promoter sequence linked to SEQ ID NO:3, which is operably linked to a coding sequence, wherein said promoter sequence is heterologous to SEQ ID NO:3; and wherein said SEQ ID NO:3 increases the expression level of the coding sequence in the transgenic seed compared to a transgenic seed transformed with an expression cassette comprising the promoter sequence operably linked to the coding sequence and lacking the polynucleotide of SEQ ID NO:3.

12. The transgenic seed of claim 11, wherein said coding sequence is heterologous to said SEQ ID NO:3.

13. The transgenic seed of claim 11, wherein said seed is selected from the group consisting of monocot and dicot seeds.

* * * * *

SEQUENCE LISTING

```
<160> NUMBER OF SEQ ID NOS: 19

<210> SEQ ID NO 1
<211> LENGTH: 470
<212> TYPE: DNA
<213> ORGANISM: Arabidopsis thaliana
<220> FEATURE:
<221> NAME/KEY: COX5c-1 Promoter
<222> LOCATION: (1)..(470)

<400> SEQUENCE: 1
gaattcaata cgaatagtta catttgtat ttttgattac tgttgtttca tgtttgtacc      60 ttttaccaa tttaatgccc tatactattt ccgttgaagc tttaaattca caagttggtt    120
atatattagg tgagctgaaa atatcatttg ggccatttac ttcatacagt tgagaaaata    180
```

```
ttcaatttga cacgttttt ttaatatag ttgtatcgtg ttttcttatt tattagaatt        240
aatttctgtc aatataataa tttgtggttt tgctttcttt gggtcgcatc aaatgttagg        300
tgttttgaaa ttttgatgat attattattt ttagacaaaa ttgactggag ttgaacagta        360
atgggccggt ctcagatgtt agcccaatag gttgacagag aaaatgtatg atccatgaga        420
gtgactaaat taaattgatt aatctcttgc gcacacctga atcctcgtct                 470
```

```
<210> SEQ ID NO 2
<211> LENGTH: 43
<212> TYPE: DNA
<213> ORGANISM: Arabidopsis thaliana
<220> FEATURE:
<221> NAME/KEY: COX5c-1 Exon 1
<222> LOCATION: (1)..(43)

<400> SEQUENCE: 2
tcattcgttc cggtcgtcgt ctacacctcc acactccgac ttg                         43
```

```
<210> SEQ ID NO 3
<211> LENGTH: 677
<212> TYPE: DNA
<213> ORGANISM: Arabidopsis thaliana
<220> FEATURE:
<221> NAME/KEY: COX5c-1 Intron
<222> LOCATION: (1)..(677)

<400> SEQUENCE: 3
gtaaatcccc agactcatct ctctctctcc ttttcttttg atttctagat ttgctagttt        60
gtttcgattg ttcttctaga tagaaattaa cgagtgattt ttgatttaac cgattcgcat       120
caatgcccct tcttcttatt gcgtcgatct catggatcgg gatccatcgt tcctctatct       180
gatttctctt gtgggaaaga atttcaagct ttatggtttt gtagtaatga acgtttatca       240 tttcgttcg agggaagatt tttaaacttt cgttatgcgg attctggata ttaggctgtt       300 ttttttttt ttttttaatc gattgaagga tgtcaattta tagattgggc tgtagattgc       360
tagtttatgt cattgatatt gaattgtaag ttttcgatc ttccagtcat acaaatcact       420
aattgcctca agataggaaa atccattggc agtatataga tggagttcat atcttaagca      480
caggtttata tggtcattac atttctagct tttgtttgtt aggactgatt catgttgggt      540
ttttggggtt attctttata acgggtcatg cttgtatata tgtagtatca atacatttct      600
gatttgtggt tatgcttgat gcaaaaaaga tccaatcttt cgagttggta gtgagttaca      660
tttgttactt ttggtag                                                    677
```

```
<210> SEQ ID NO 4
<211> LENGTH: 21
<212> TYPE: DNA
<213> ORGANISM: Arabidopsis thaliana
<220> FEATURE:
<221> NAME/KEY: COX5c-1 Exon 2 non-coding region
<222> LOCATION: (1)..(21)

<400> SEQUENCE: 4
gttgagaaga agaaagaaga g                                                21
```

```
<210> SEQ ID NO 5
<211> LENGTH: 1617
<212> TYPE: DNA
<213> ORGANISM: Arabidopsis thaliana
<220> FEATURE:
<221> NAME/KEY: COX5c-2 Promoter
```

<222> LOCATION: (1)..(1617)

<400> SEQUENCE: 5

| | | | | | |
|---|---|---|---|---|---|
| gaattccaca | gtgcatttat | aatcctagtc | aagtacacaa | acatgacatt | aacacaacca | 60 |
| cacgcctgaa | atacacttaa | tggtccatta | agattaaagt | catattgtac | cacgaaacgg | 120 |
| aagctataat | tccctttctc | tttggtgatt | cttcggttgt | gcgtttcgta | tactctcttg | 180 |
| ggatctttaa | cagcttgaaa | caacaaacaa | agcatagatt | cccattggtt | cctattaatt | 240 |
| gaatctccaa | cgaacactag | cctcttgcct | ctaatcattt | ccagcatctt | tgtagcattg | 300 |
| aacctaaact | cacacatacc | acaatttcca | attcaggacc | atgaattgca | ttcctactta | 360 |
| ttcagagaga | ttaagtgctc | agtggaacta | tgaatcccac | ttatcatcat | cagtcactat | 420 |
| caccaaccac | tactacttca | atagagagat | cttcttaaag | gcctacgagg | aaaacaacaa | 480 |
| aattagaaag | aagaaattaa | acctgggagc | atgacaatcc | tgaggctccc | atctccaatt | 540 |
| catgtaatta | agatccaatc | ttccattgct | ttgacaacca | aatccttcat | cgataaaact | 600 |
| agcctatgaa | tccacatggc | aaaagaggac | aagacgcatt | tgtgtacaat | ggataatcac | 660 |
| tatcgtaaac | ccacttccct | ttcgtaacat | cacattcttc | gattctcttc | tctgtcttct | 720 |
| tatcttcacc | attgttgctc | ggaagttcaa | tcactttaat | cgaagttaaa | ttagcaattt | 780 |
| ccctaacttc | cttaaccaaa | ctctcgccgc | taatcttctg | ctcaaaaaca | gaaattttg | 840 |
| aagacccgga | agtgttttcg | ggtgaattga | atgggtaga | gatcagaatc | ggacttgctt | 900 |
| gaggagaaac | tgaagaatcg | gaatggcgg | caatagggct | taaatcgatc | tggaagttag | 960 |
| cttctggtgt | tgggtaaaga | gaagagttag | atttgagtaa | ggaagaggag | aagaaagtga | 1020 |
| agaaaacaat | ggcggaagag | attattgtga | tgatgaatgc | taagactctt | gtggacttca | 1080 |
| cagagaaact | tctttgtctc | tccatcttct | atctctttat | ttattttttc | tctgtaactg | 1140 |
| ttataagtta | gttaagaaaa | aacagtttca | taattatctg | taatcagaga | aatttgaaat | 1200 |
| cgaaaaatgg | aactgtttga | gaaaaggatt | gaaattttgg | agtcgacaaa | ggtggttgaa | 1260 |
| ttagtggggt | atagaggaga | gattcggtga | agaaatgata | atgacgttct | tacaaactcg | 1320 |
| tgagctcatg | aattttacaa | taattaacgg | aacagaggga | aagataatga | ttatttaaaa | 1380 |
| aagttcagga | ttaggaaatt | agtttagtgt | gttgacagat | tggatttggc | attattaacg | 1440 |
| tggtgggaca | cactcgggga | acacgagcag | cgaatggttt | actttttttaa | aaagcaaatt | 1500 |
| ccataaaatg | cccattgaag | aaataagaga | tcaggcccat | gtttaaggcc | caataagaca | 1560 |
| caaatggagt | agagaagtga | ttatctgctt | acgcaacttc | ttcaatcacc | caccatt | 1617 |

<210> SEQ ID NO 6
<211> LENGTH: 49
<212> TYPE: DNA
<213> ORGANISM: Arabidopsis thaliana
<220> FEATURE:
<221> NAME/KEY: COX5c-2 Exon 1
<222> LOCATION: (1)..(49)

<400> SEQUENCE: 6
tcgttttcgt cgtgagcttc tgtctcgttc atctacacaa tctgactcg                49

<210> SEQ ID NO 7
<211> LENGTH: 580
<212> TYPE: DNA
<213> ORGANISM: Arabidopsis thaliana
<220> FEATURE:
<221> NAME/KEY: COX5c-2 Intron
<222> LOCATION: (1)..(580)

<400> SEQUENCE: 7

```
gtaaagtcca tattcttccc ttgatgataa ttgttgtttc ctttatgatt ttgtggtgat    60
tttcgttata dataggtggc ggattgtgaa gttacgatta atttttatca gattcgaatc   120
catttctcgt ttttttccc gtgtagatcg gtgtgcttaa gatcggaatt tctcgtttaa   180
atcttccgtt gatttagatt tgatgctctt agtgttgtga tgctttgaaa cgttaatcct   240
tttcttcggg agaaatgcca attttatttt cagtatctgg atcctgtgga ttagggttct   300
tgtatcattt tgggaataaa ttcaaagcct tgatatctt cctttgaata gagacgtagt   360
taagaggtta dacagaaaat ggatcgaaat tgtacatgtt tatgtgtata tatagactcc   420
aagtgcaaac cagtagaaat taagagatca ggtagattag tgtgtgtgtg tgtatagatg   480
ttttattggt tgtcaataaa gttttcagct ttaggaatcg tgagcattgt gaaagtatca   540
attatgttag tattgactct atgattaaaa tgtgtgctag                         580
```

<210> SEQ ID NO 8
<211> LENGTH: 11
<212> TYPE: DNA
<213> ORGANISM: Arabidopsis thaliana
<220> FEATURE:
<221> NAME/KEY: COX5c-2 Exon 2 non-coding region
<222> LOCATION: (1)..(11)

<400> SEQUENCE: 8

```
gttgagaaga a                                                         11
```

<210> SEQ ID NO 9
<211> LENGTH: 1082
<212> TYPE: DNA
<213> ORGANISM: Arabidopsis thaliana
<220> FEATURE:
<221> NAME/KEY: COX5c-3 Promoter
<222> LOCATION: (1)..(1082)

<400> SEQUENCE: 9

```
aagagatggg aagagtttct tacgttcagg agagaacaca agaacgtctt gcttccgttg    60
attcgttccc ggagaaagat catgatcgaa tctaaagatt ccggtaaaga atacatacaa   120
tcgtatgtag atactctgct cgatcttgag cttcctgatg agaagaggaa actaaacgaa   180
gacgagatcg tgagtttatg ctctgagttt ctcaacgccg ggactgatac aacagcgacg   240
acacttcaat ggataatggc gaatctgtga gaaaccagga aattcaaaag aggttatacg   300
aagagataaa aagtgtaatc ggtgaagaag aagagaagga gattgaagaa gaagagatga   360
agaagatgcc gtatcttaaa gctgtcgtgt tagaaggtct ccggttacat ccaccgggac   420
atttgttgtt accacacaga gtaagtgaag acactgagct aggaggatac agagttccaa   480
agaaagggac gtttaatatc aatgtggcga tgatagggag agatccaaca gtgtgggagg   540
agccaatgga gtttaagccg agagattca tcggagaaga taagaagtt gatgttactg   600
gaagtagagg gataaagatg atgccgtttg gagcaggaag gaggatctgt ccagggattg   660
gatcggccat gttgcatttg gagtattttg tggtgaattt ggttaaagag tttgagtgga   720
aagaagttga aggttatgaa gttgacttgt ctgagaaatg ggagttcact gttgttatga   780
agtatcctct taaagctctt gctgtgacaa gaaggaagga gaagacacat atcgtcatgg   840
cttagagaca gagtagcaga ttgatttctt ggggatgttt tgttctttta gtttttcagt   900
tttttttttt tttggttttc tagagtgttt ttggttcaat ctgttgtggt agaaacgttg   960
```

```
tcgtttcaat aaaggcagcc atttattgaa acgttgtcgt ttagatgcct ctcattttg    1020 ttgaaagccc tagaaaatgg aattagacgt ataaattgat ttcatctttc tcagcttttg    1080
ct                                                                   1082

<210> SEQ ID NO 10
<211> LENGTH: 65
<212> TYPE: DNA
<213> ORGANISM: Arabidopsis thaliana
<220> FEATURE:
<221> NAME/KEY: COX5c-3 Exon 1
<222> LOCATION: (1)..(65)

<400> SEQUENCE: 10
aaacgcagat aaacaggttt ctttctgatt cttcttcgta ttggaacata caattataca     60
attgg                                                                 65

<210> SEQ ID NO 11
<211> LENGTH: 1034
<212> TYPE: DNA
<213> ORGANISM: Arabidopsis thaliana
<220> FEATURE:
<221> NAME/KEY: COX5c-3 Intron
<222> LOCATION: (1)..(1034)

<400> SEQUENCE: 11
gtataaccat tttcttggat ttcagtgtat gattcctttt aatgttcaaa gttctctgct     60
ttctcttgcg taattttgct ctctgttttt tttttgtctt catctgtata atggaatctc    120
ccgaaaaaac tcgaagttta taaactggat tgattccttt cttctccatt gtggtcttag    180
gtttcgaaag tttctcactt tagacttgtg ttagctctag aatgcttgta tgatatgttt    240
gtgacattgt ggtggagatg atgaatgtta agtaaaaggt ctgagtaggt tatgagtaaa    300
gtgtgtagct tttgatttta atttagtttc gaggagacaa ttttttaact aataggaga     360 gggcccttgt ccatgccttg agtcatggca tctgtggctc cgcaacctct ccaacaatga    420
acctgattca ccacgtgctt gtgtgtgcaa tctgatgggt cgatttttaa aggcttgggg    480
ttgctttcta ttattgattg ccaatctaga attctcccta tatacattgg tctccttgtg    540
cttctttatc atcaattagc tgccctcata agtcctgcac tgatcaaaga cctccttgac    600
tgatccacgc gaaagtatct aaatagttct ttgtattgct atgttgaagt ttgaagcttt    660
ttgacaaagc ttgtttgata taggcattgc ttgtggatga tgtttatgat tccctcatta    720
ttgtatgtgt ggactacaga actattcatg tattagcatt tacccttttg tggttaagct    780
gaagaagtat accataccct ctagtgtttg tttgattggg tttttcactg tggccattag    840 agtgttaag ataagtactc tgtttgtcga tactctagga tctctctttc aagtgggttt    900
gatttgaaga cgtattatat gtgtatatat aaccgaagaa taatgttatg ttttgctaaa    960
tgttgatgtt tagattatca aagagaatgg attttgtat attcatgatc tattgcaatg    1020
tttgattggt ttag                                                      1034

<210> SEQ ID NO 12
<211> LENGTH: 24
<212> TYPE: DNA
<213> ORGANISM: Arabidopsis thaliana
<220> FEATURE:
<221> NAME/KEY: COX5c-3 Exon 2 non-coding region
<222> LOCATION: (1)..(24)

<400> SEQUENCE: 12
```
tgtgagcagg agagtggcaa agag                                               24

<210> SEQ ID NO 13
<211> LENGTH: 27
<212> TYPE: DNA
<213> ORGANISM: Artificial sequence
<220> FEATURE:
<223> OTHER INFORMATION: COXC32

<400> SEQUENCE: 13
ggcagatctc tcttctttct tcttctc                                            27

<210> SEQ ID NO 14
<211> LENGTH: 27
<212> TYPE: DNA
<213> ORGANISM: Artificial sequence
<220> FEATURE:
<223> OTHER INFORMATION: COXC41

<400> SEQUENCE: 14
gcgtctagat tcttctcaac ctagcac                                            27

<210> SEQ ID NO 15
<211> LENGTH: 27
<212> TYPE: DNA
<213> ORGANISM: Artificial sequence
<220> FEATURE:
<223> OTHER INFORMATION: COXC33

<400> SEQUENCE: 15
ggcggatccc aagtcggagt gtggagg                                            27

<210> SEQ ID NO 16
<211> LENGTH: 27
<212> TYPE: DNA
<213> ORGANISM: Artificial sequence
<220> FEATURE:
<223> OTHER INFORMATION: COXC42

<400> SEQUENCE: 16
ggcggatccc gagtcagatt gtgtaga                                            27

<210> SEQ ID NO 17
<211> LENGTH: 38
<212> TYPE: DNA
<213> ORGANISM: Artificial sequence
<220> FEATURE:
<223> OTHER INFORMATION: COXC45

<400> SEQUENCE: 17
gcgtctagat tcttctcaac cgagtcagat tgtgtaga                                38

<210> SEQ ID NO 18
<211> LENGTH: 27
<212> TYPE: DNA
<213> ORGANISM: Artificial sequence
<220> FEATURE:
<223> OTHER INFORMATION: COXC44

<400> SEQUENCE: 18
ggctctagag ttttcgtcgt gagcttc                                            27

<210> SEQ ID NO 19
<211> LENGTH: 18
<212> TYPE: DNA
<213> ORGANISM: Artificial sequence -continued

```
<220> FEATURE:
<223> OTHER INFORMATION: gus-specific primer

<400> SEQUENCE: 19
ttggggtttc tacaggac                                                 18
```